(12) United States Patent
Mueller et al.

(10) Patent No.: US 7,279,471 B2
(45) Date of Patent: Oct. 9, 2007

(54) SELECTED CGRP-ANTAGONISTS, PROCESS FOR PREPARING THEM AND THEIR USE AS PHARMACEUTICAL COMPOSITIONS

(75) Inventors: Stephan Georg Mueller, Warthausen (DE); Klaus Rudolf, Warthausen (DE); Philipp Lustenberger, Warthausen (DE); Dirk Stenkamp, Biberach (DE); Kirsten Arndt, Biberach (DE); Henri Doods, Warthausen (DE); Gerhard Schaenzle, Biberach-Mettenberg (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 139 days.

(21) Appl. No.: 11/107,189

(22) Filed: Apr. 15, 2005

(65) Prior Publication Data
US 2005/0234054 A1    Oct. 20, 2005

Related U.S. Application Data

(60) Provisional application No. 60/570,006, filed on May 11, 2004.

(30) Foreign Application Priority Data
Apr. 15, 2004    (DE) .................. 10 2004 018 794

(51) Int. Cl.
```
A61K 31/537    (2006.01)
C07D 413/14    (2006.01)
C07D 221/20    (2006.01)
C07D 405/14    (2006.01)
```
(52) U.S. Cl. ............... 514/228.8; 514/278; 544/96; 544/130; 546/16; 546/187; 548/314.7; 548/517
(58) Field of Classification Search ............ 544/71, 544/96, 130; 514/229.5, 228.8, 278; 546/16, 546/187; 548/314.7, 517
See application file for complete search history.

(56) References Cited

U.S. PATENT DOCUMENTS 6,344,449 B1    2/2002    Rudolf et al.

2003/0236282 A1    12/2003    Hurnaus et al.
2004/0063735 A1     4/2004    Chaturvedula et al.
2006/0252931 A1 *  11/2006    Mueller et al. ............. 540/502

FOREIGN PATENT DOCUMENTS

WO    WO 03/076432 A1    9/2003
WO    WO 03076432 A1 *  9/2003

OTHER PUBLICATIONS

John J. Mallee, et al; Receptor Activity-modifying Protein 1 Determines the Species Selectivity of Non-peptide CGRP Receptor Antagonists; The Journal of Biological Chemistry; vol. 277, No. 16, Apr. 19, 2002, pp. 14294-14298; The American Society for Biochemistry and Molecular Biology, Inc.

* cited by examiner

*Primary Examiner*—Joseph K. McKane
*Assistant Examiner*—Joseph R. Kosack
(74) *Attorney, Agent, or Firm*—Michael P. Morris; Mary-Ellen M. Devlin; Alan R. Stempel

(57) ABSTRACT

The present invention relates to the CGRP antagonists of general formula

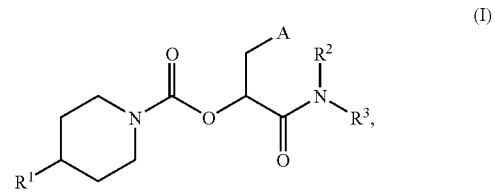

wherein A and $R^1$ to $R^3$ are defined as in claim 1, the tautomers, the diastereomers, the enantiomers, the hydrates thereof, the mixtures thereof and the salts thereof and the hydrates of the salts, particularly the physiologically acceptable salts thereof with inorganic or organic acids, pharmaceutical compositions containing these compounds, the use thereof and processes for the preparation thereof.

7 Claims, No Drawings

SELECTED CGRP-ANTAGONISTS, PROCESS FOR PREPARING THEM AND THEIR USE AS PHARMACEUTICAL COMPOSITIONS

The present invention relates to the CGRP antagonists of general formula

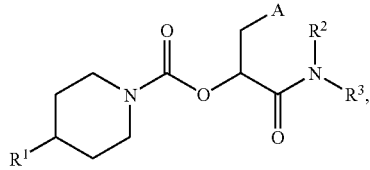
(I)

the tautomers, the diastereomers, the enantiomers, the hydrates thereof, the mixtures thereof and the salts thereof as well as the hydrates of the salts, particularly the physiologically acceptable salts thereof with inorganic or organic acids, pharmaceutical compositions containing these compounds, their use and processes for preparing them.

In the above general formula (I)

A denotes a group of formula

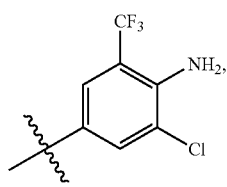
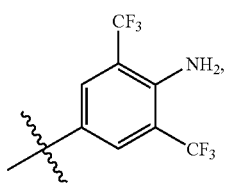
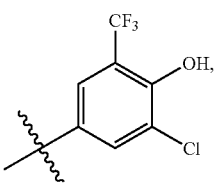
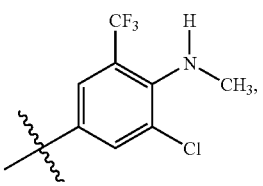
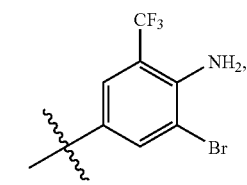
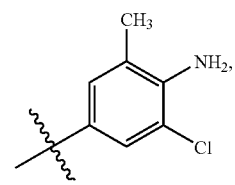
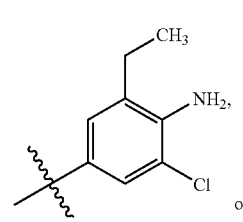
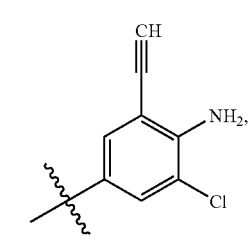
or the group

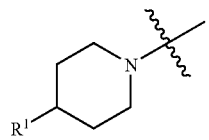

denotes a group of formula

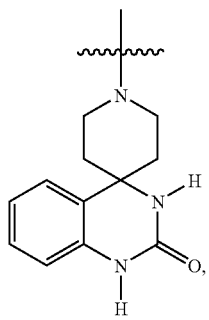
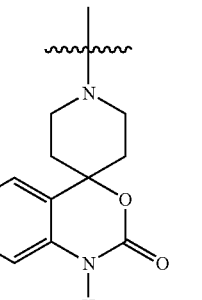
or
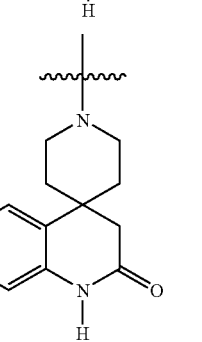
and

—NR²R³ denotes a group of formula

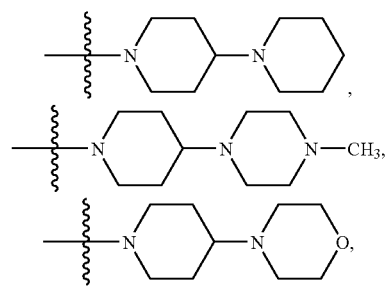

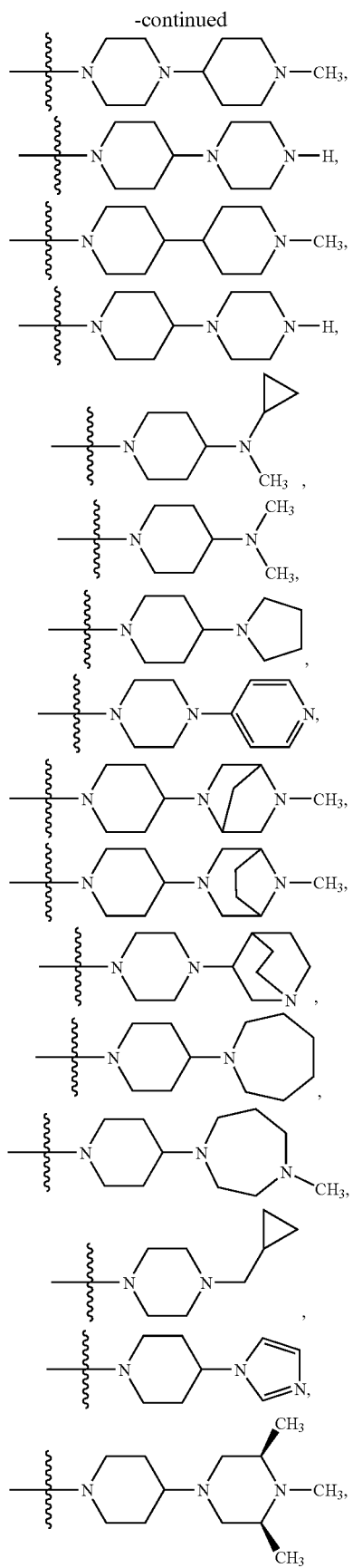
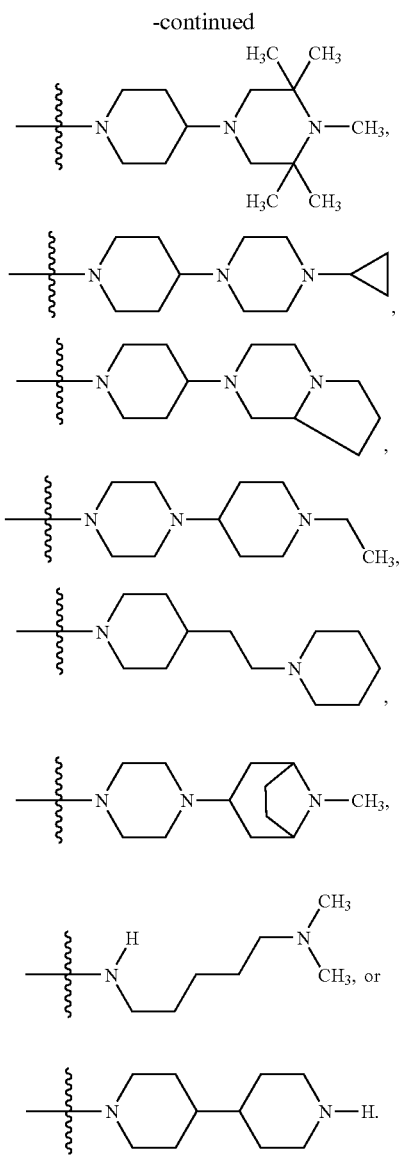
Particularly preferred compounds of the above general formula (I) are as follows, for example:
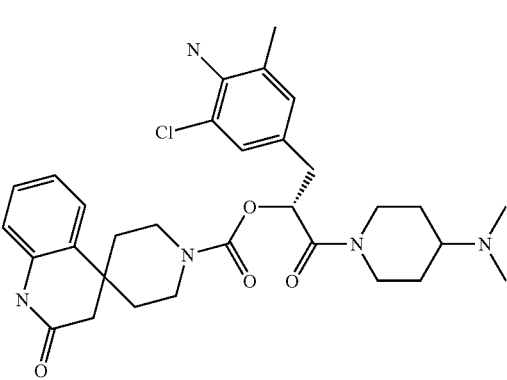

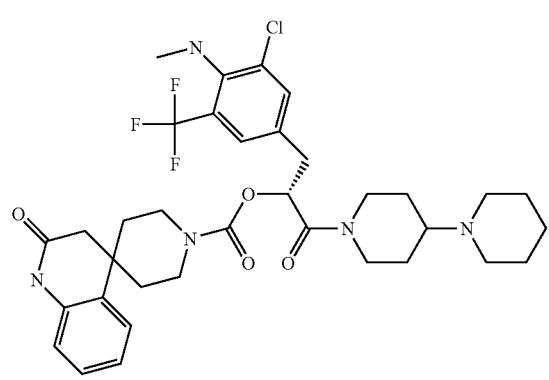
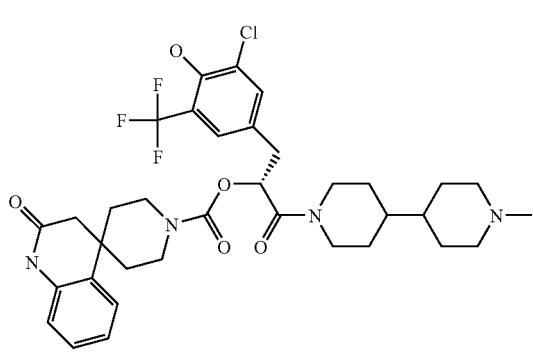
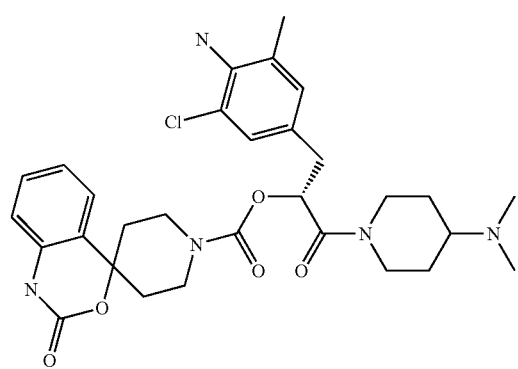
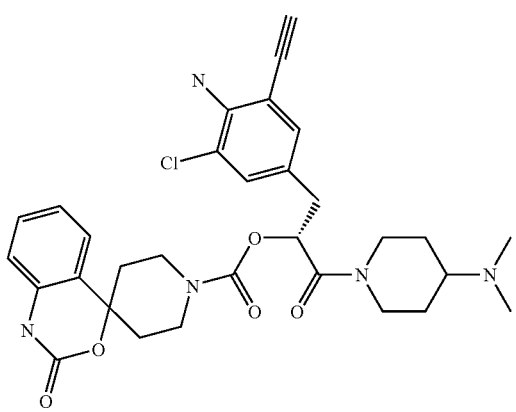
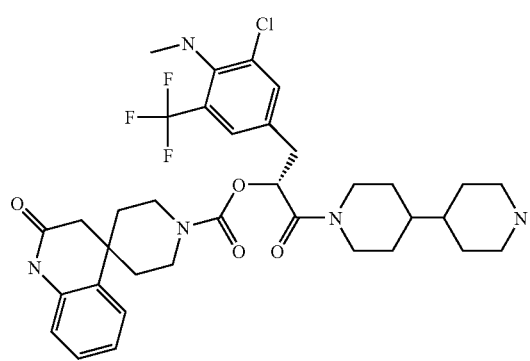
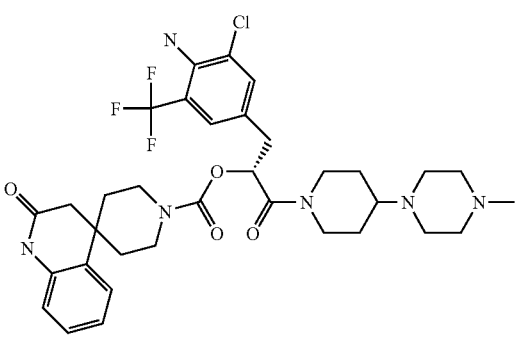
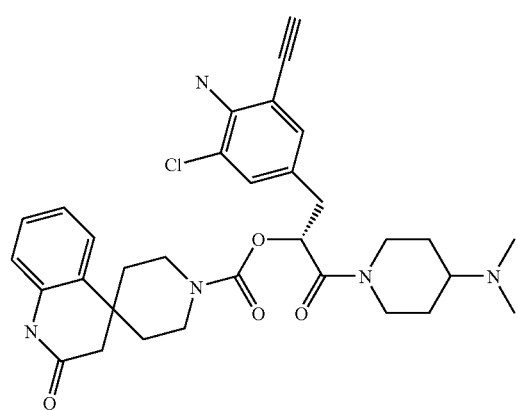
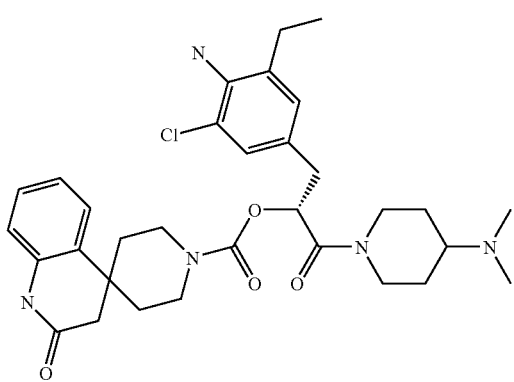

-continued

-continued
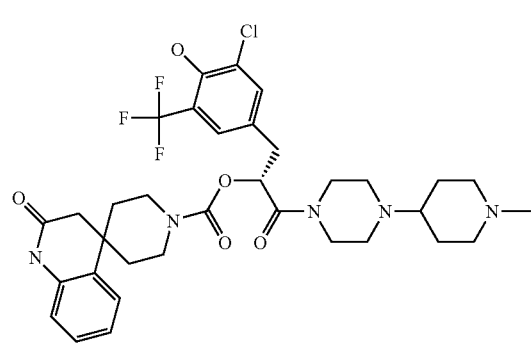
18
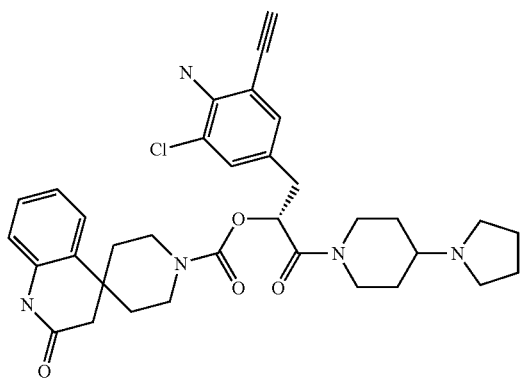
19
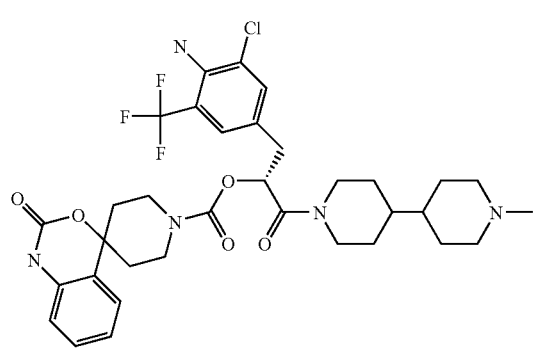
20
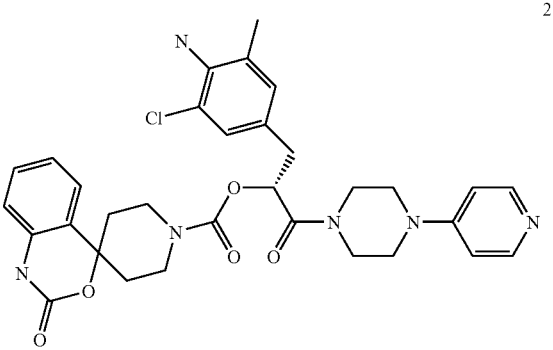
21
-continued
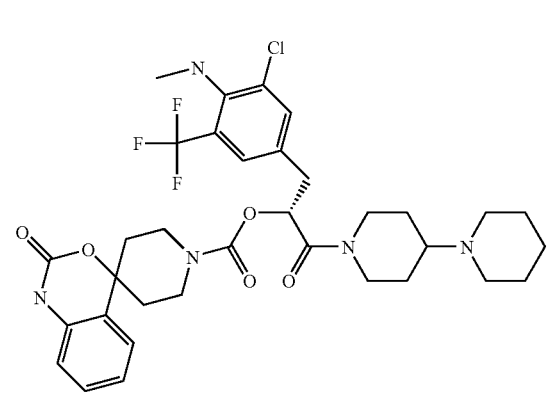
22

26
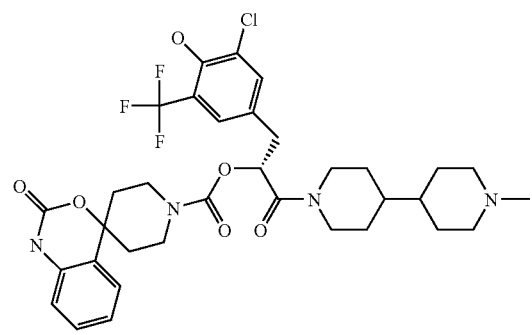
27
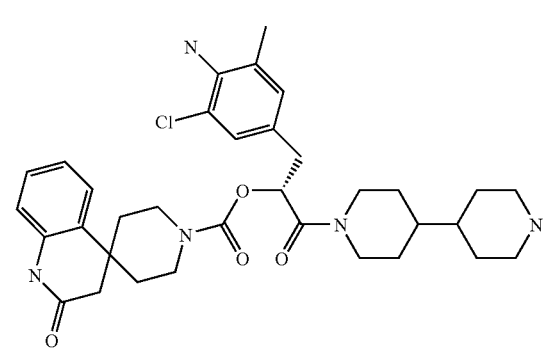
28
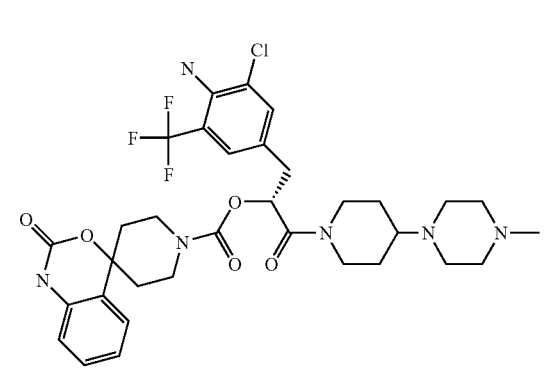
29
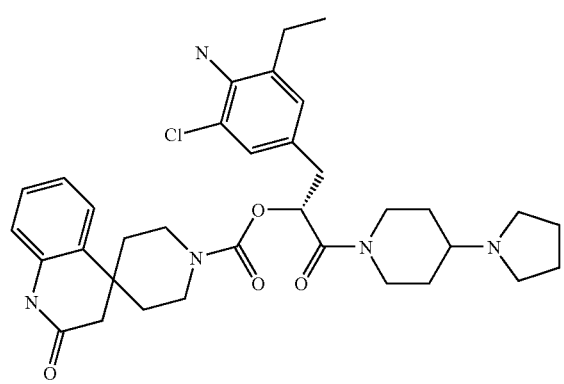
30
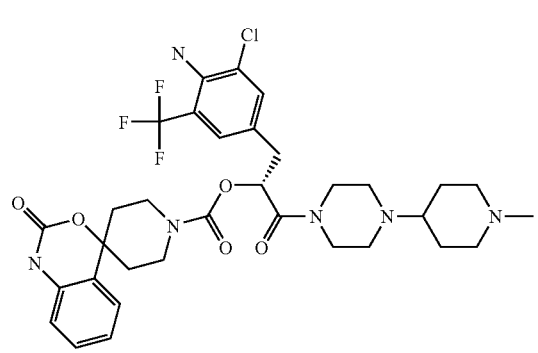
31
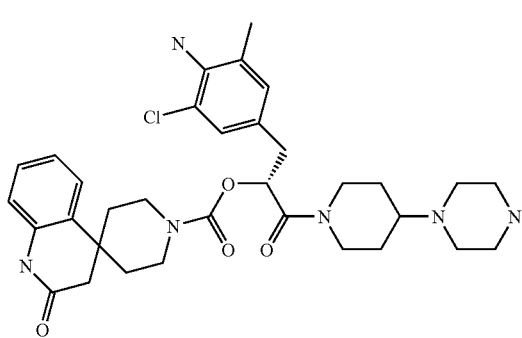
32
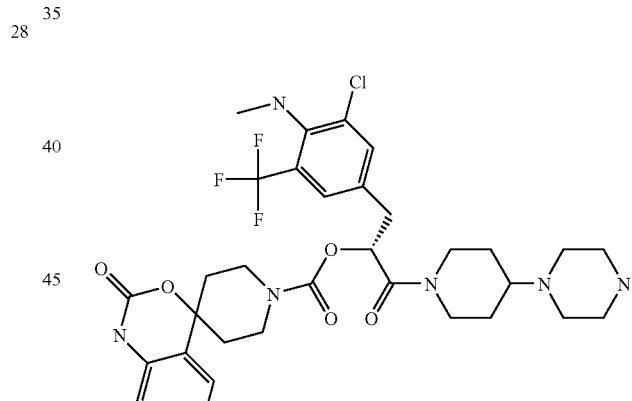
33
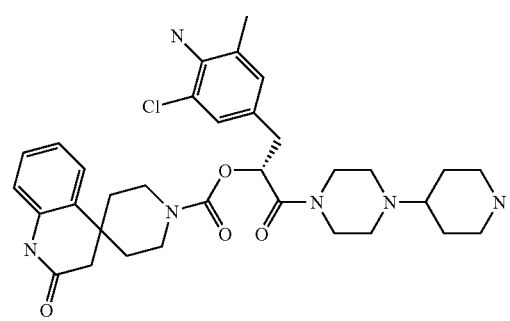

-continued
34
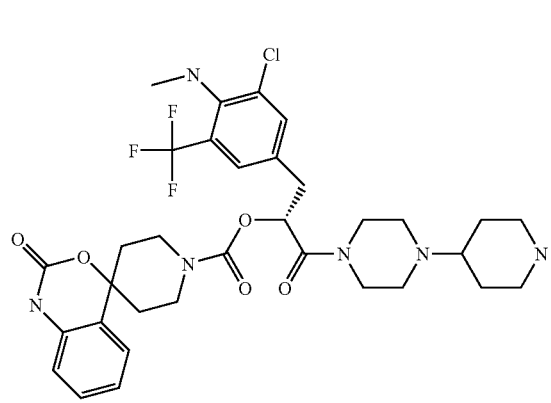
35
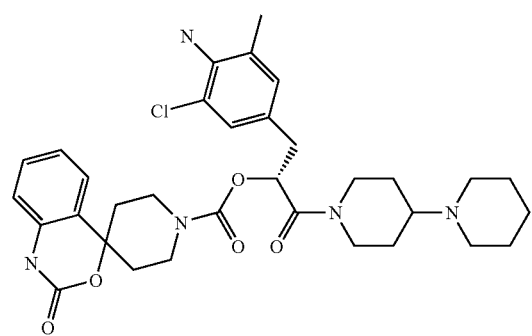
36
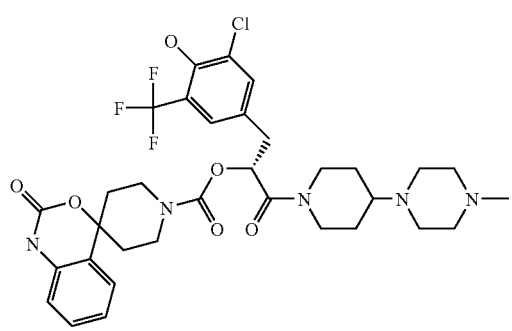
37
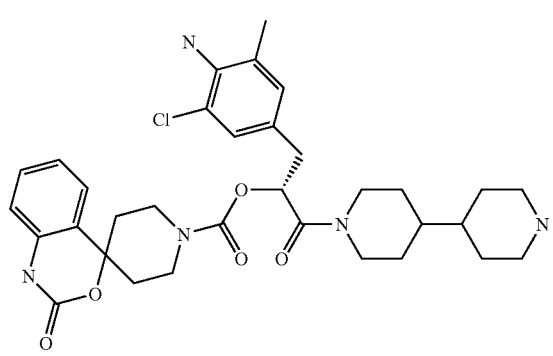
-continued
38
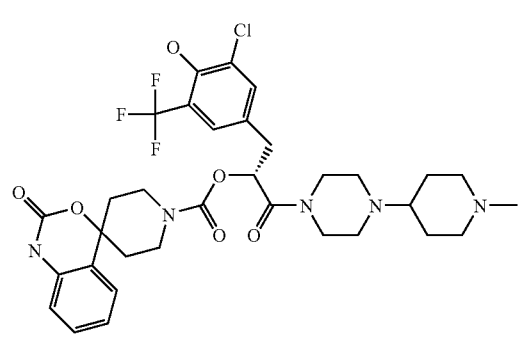
39
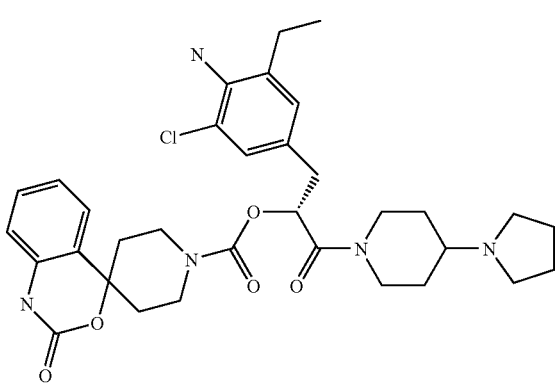
40
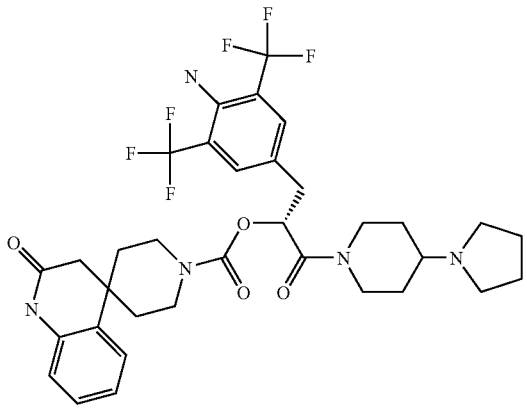
41
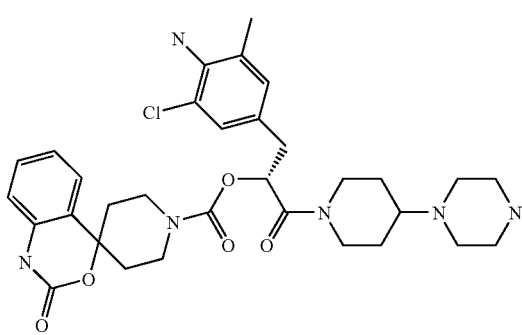

42
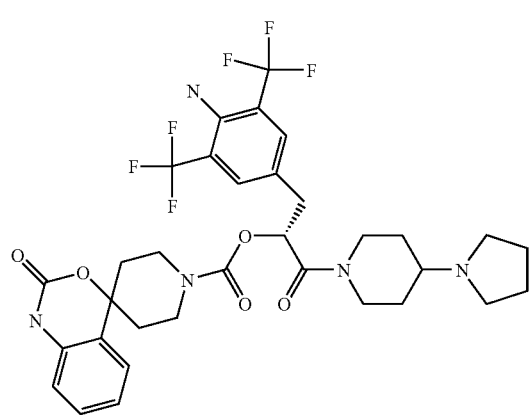
43
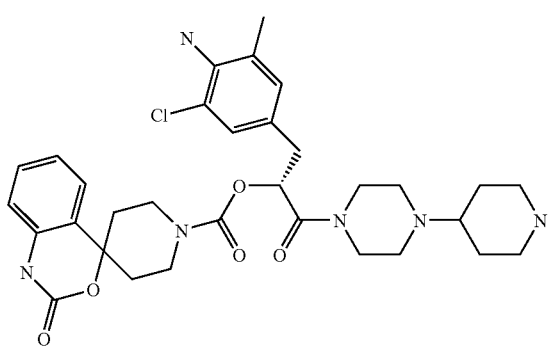
44
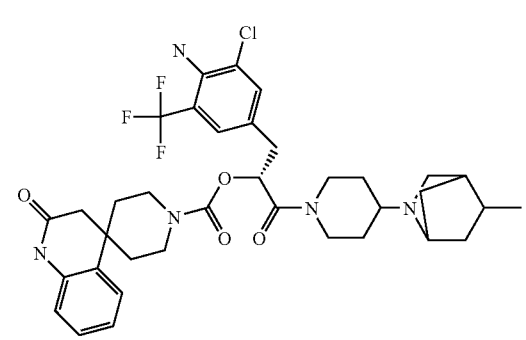
45
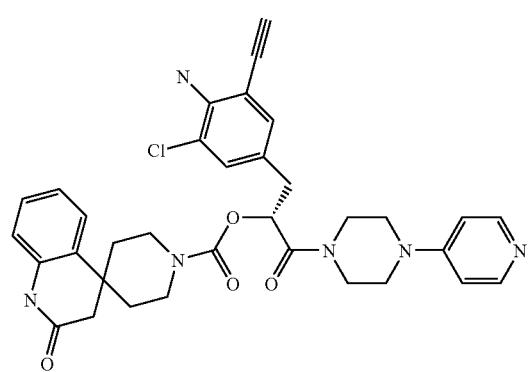
46
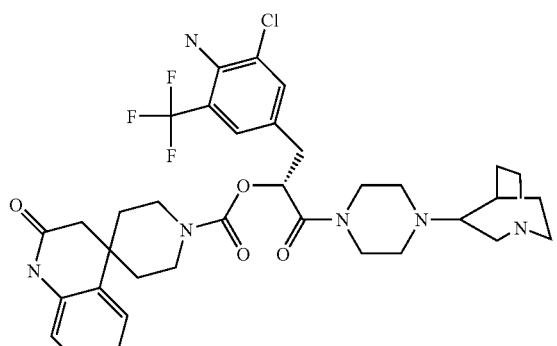
47
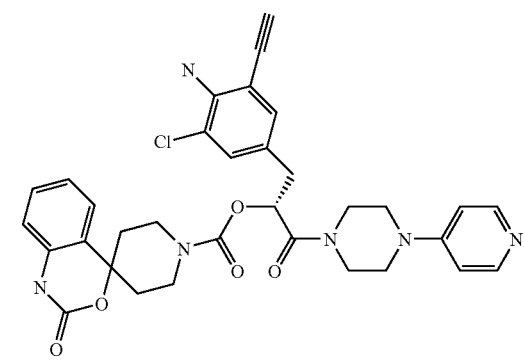
48
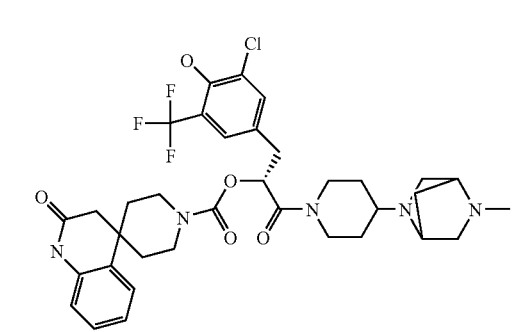
49
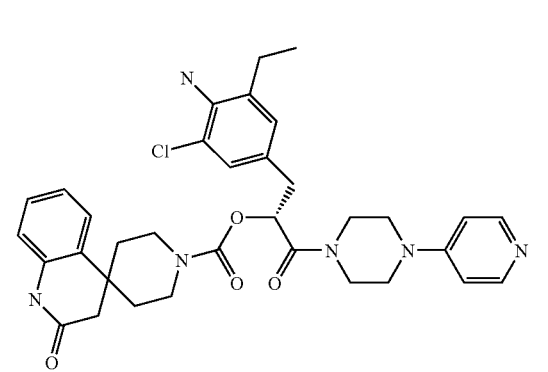

50
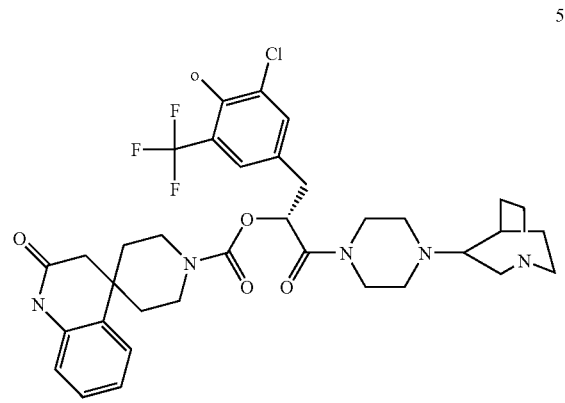
51
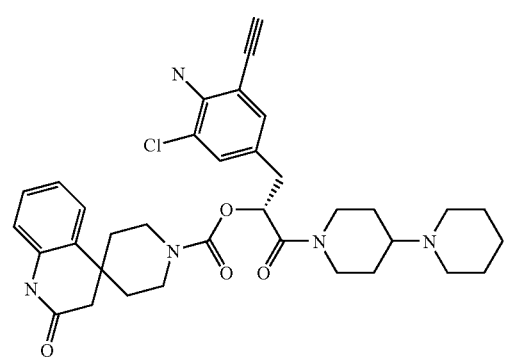
52
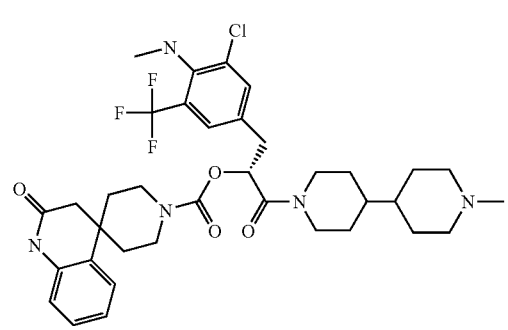
53
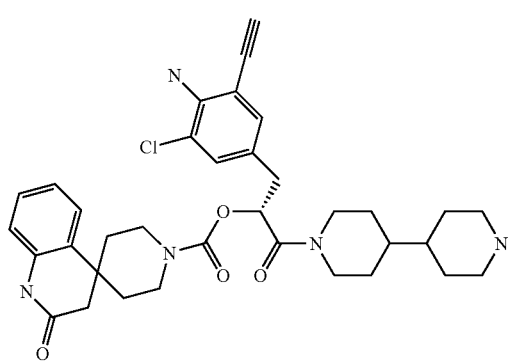
54
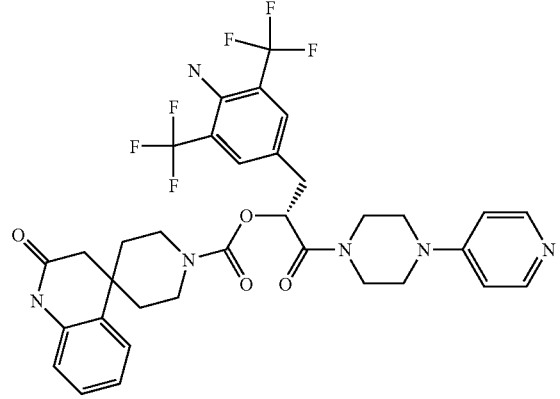
55
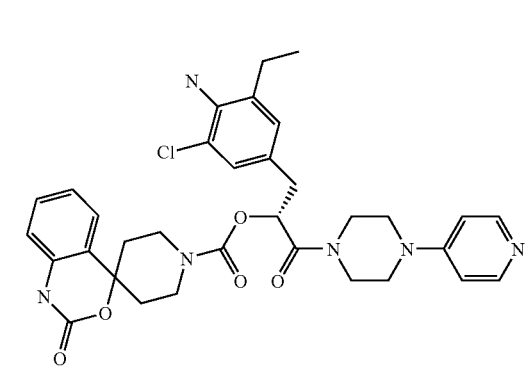
56
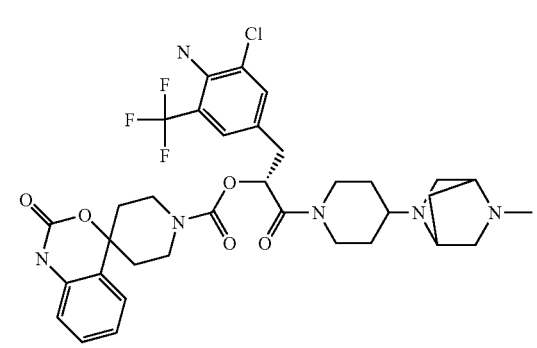
57
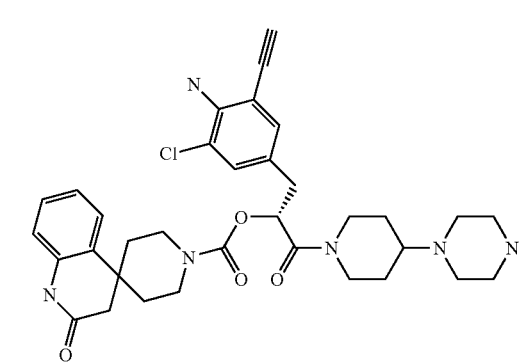

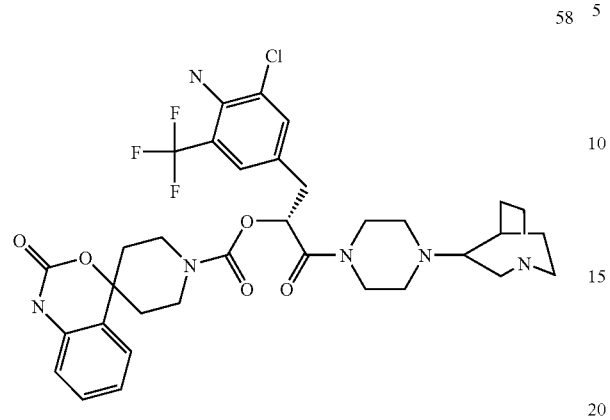
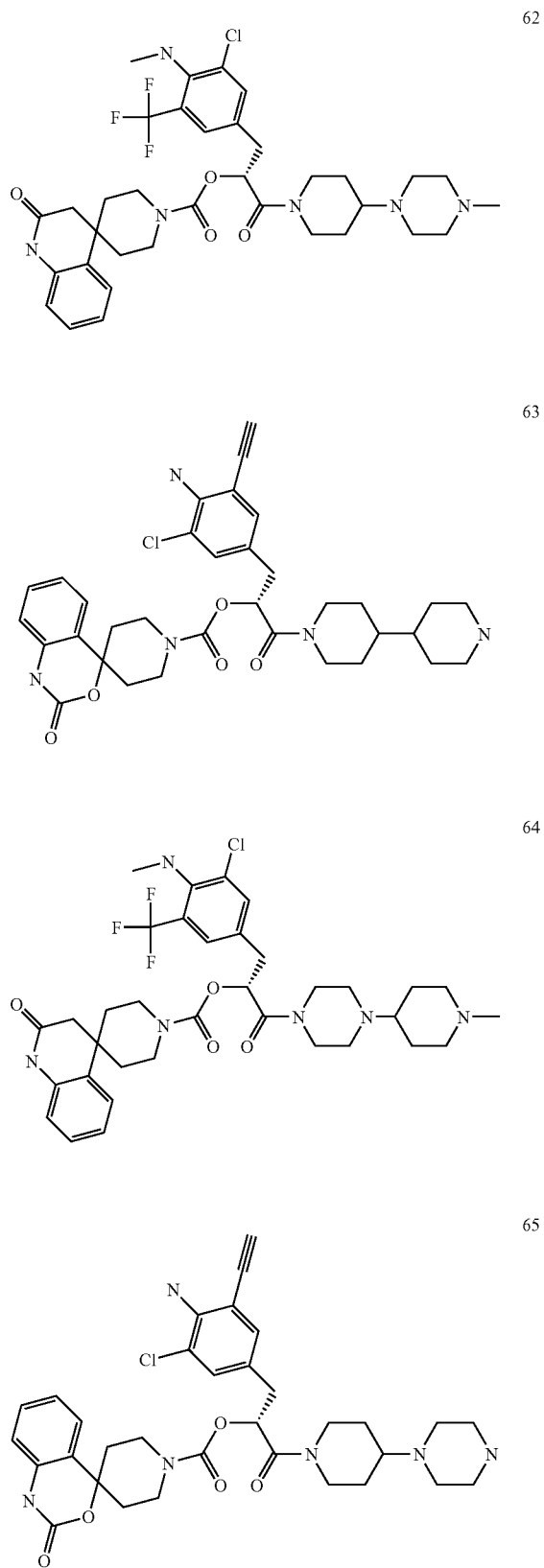

-continued
66
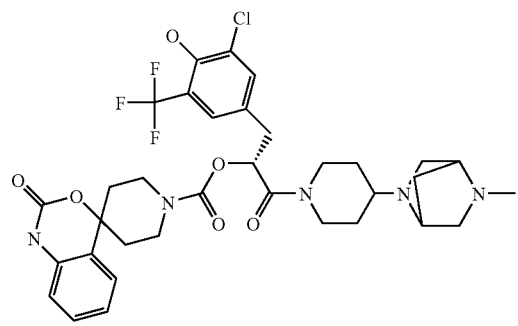
67
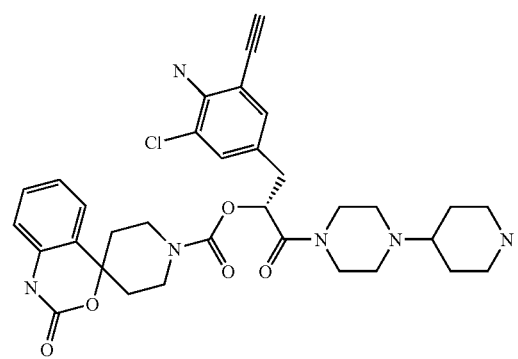
68
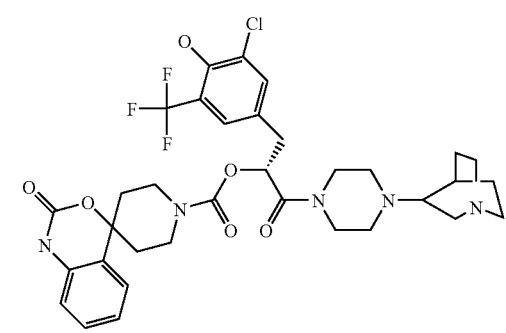
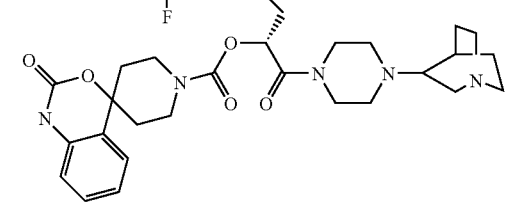
69
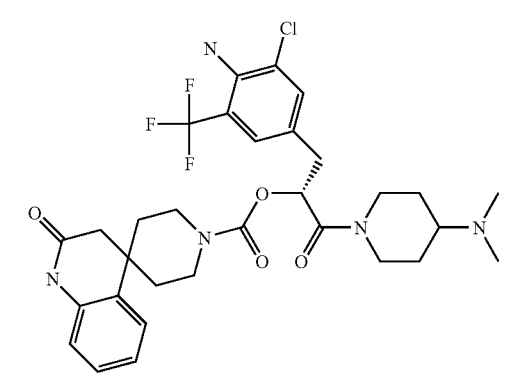
-continued
70
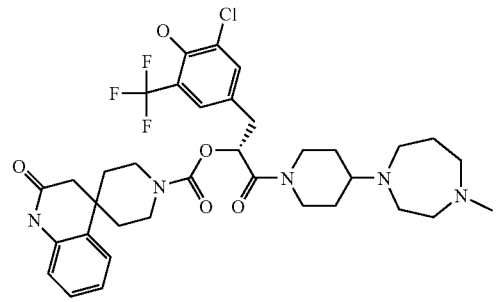
71
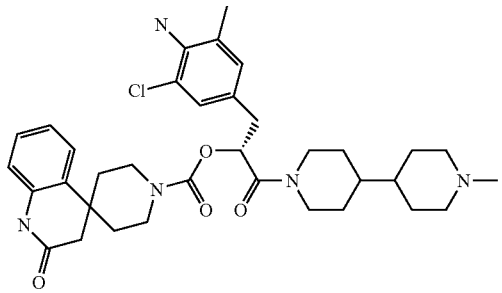
72
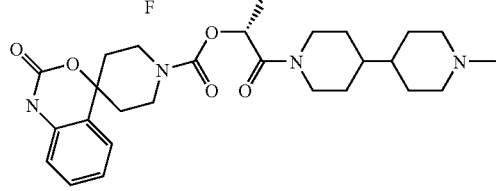
73
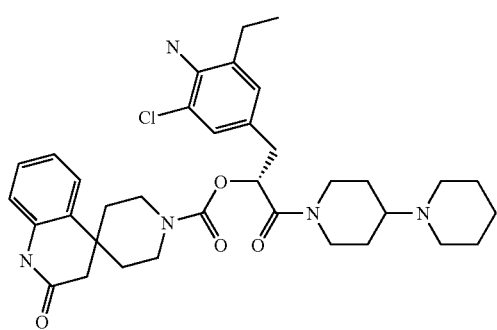
74
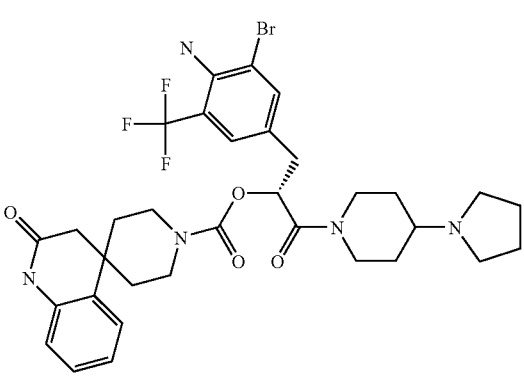

-continued

84
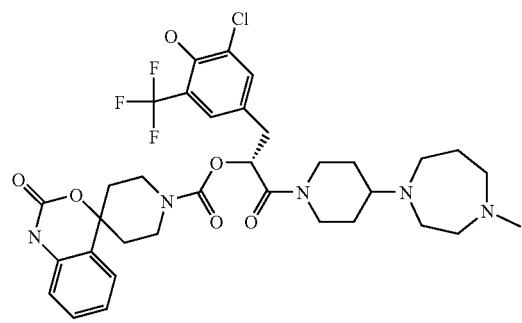
85
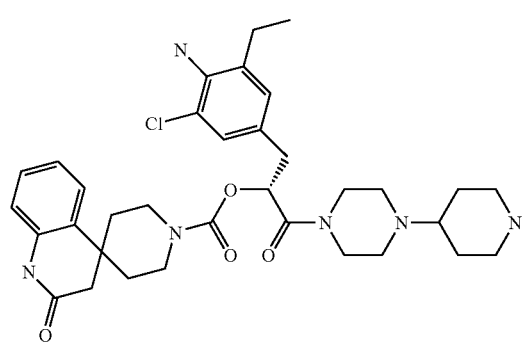
86
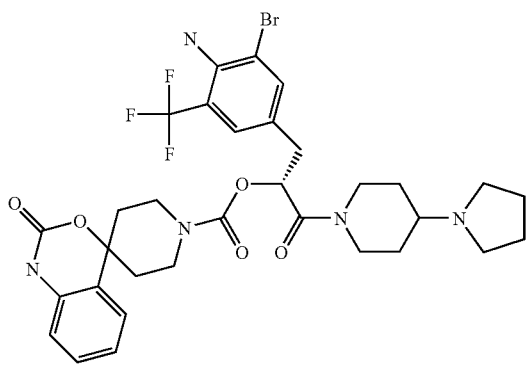
87
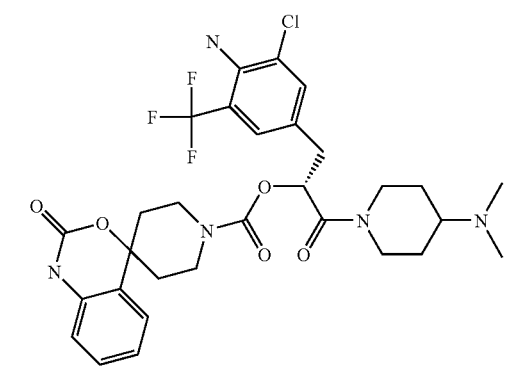
88
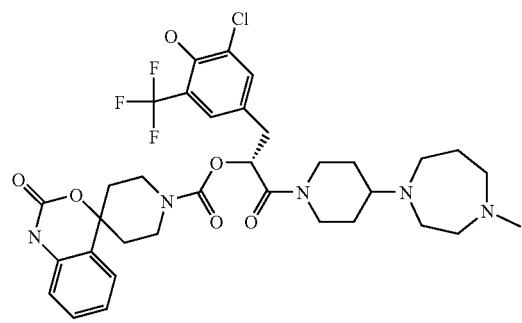
89
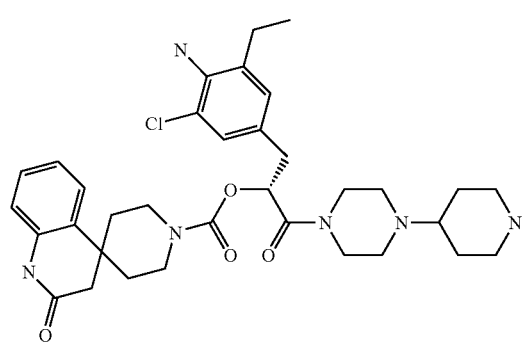
90
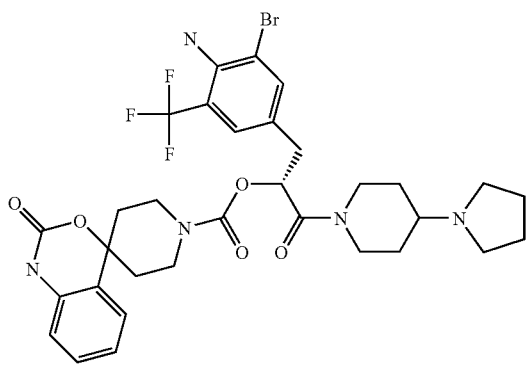
91
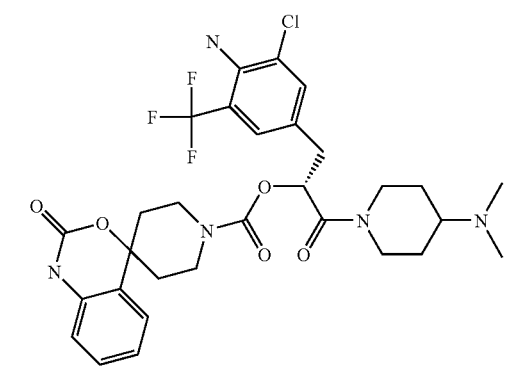

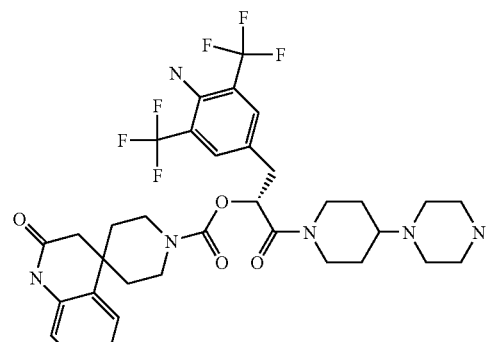
92
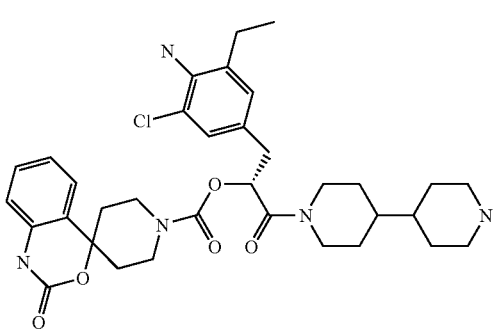
93
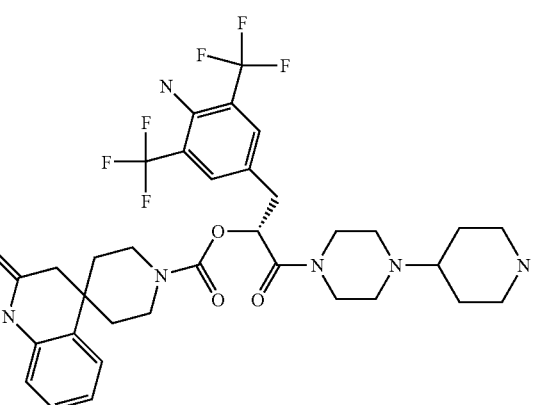
94
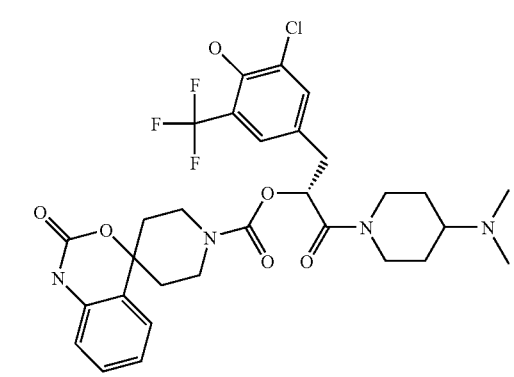
95
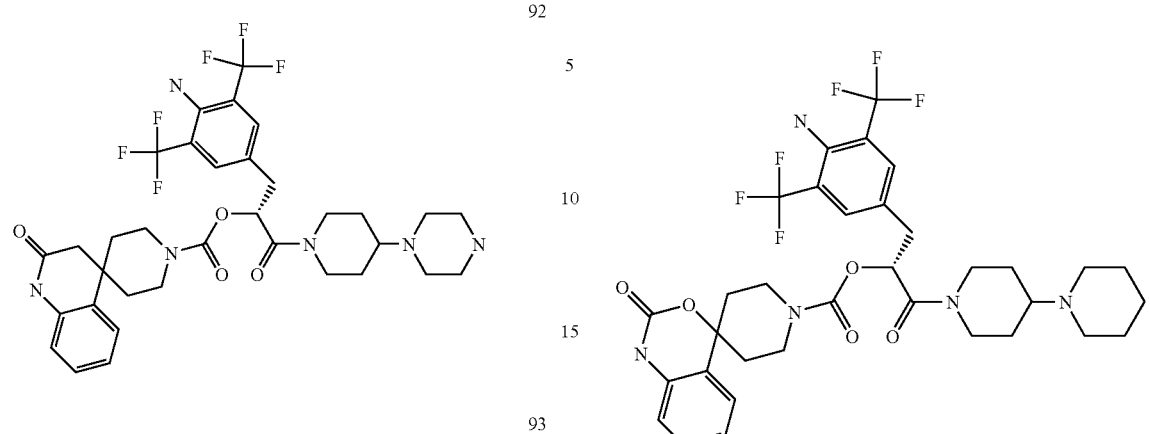
96
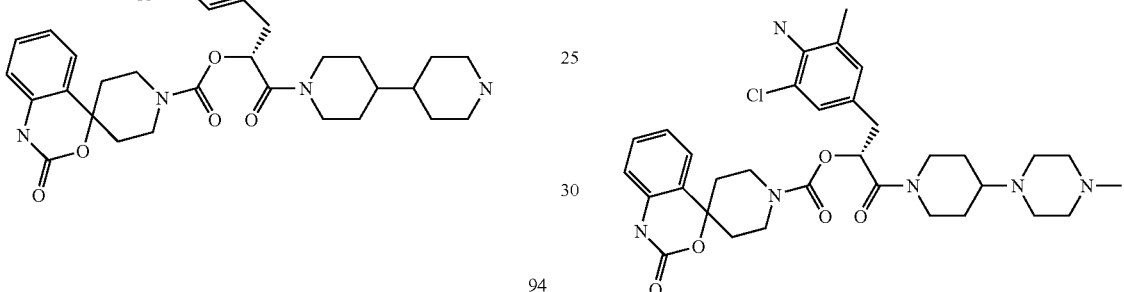
97
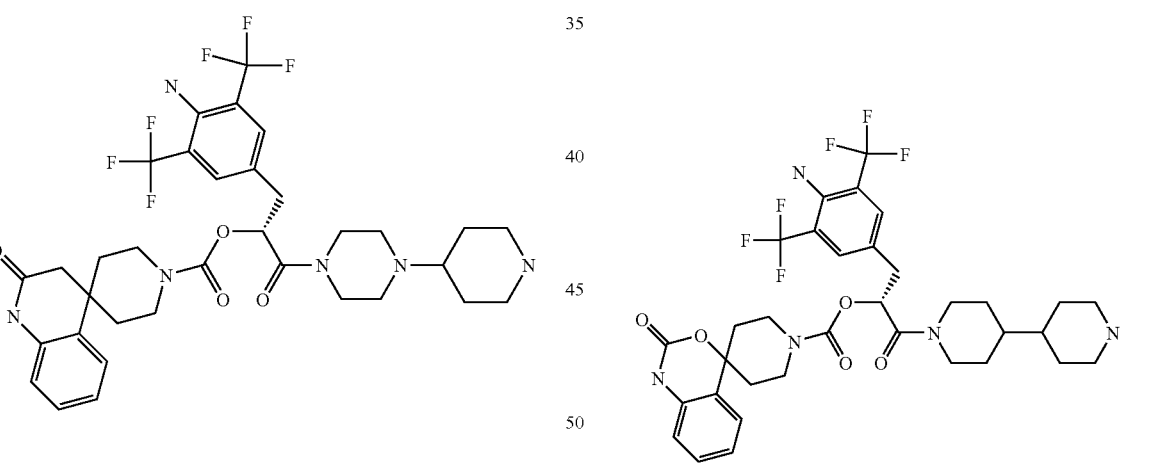
98
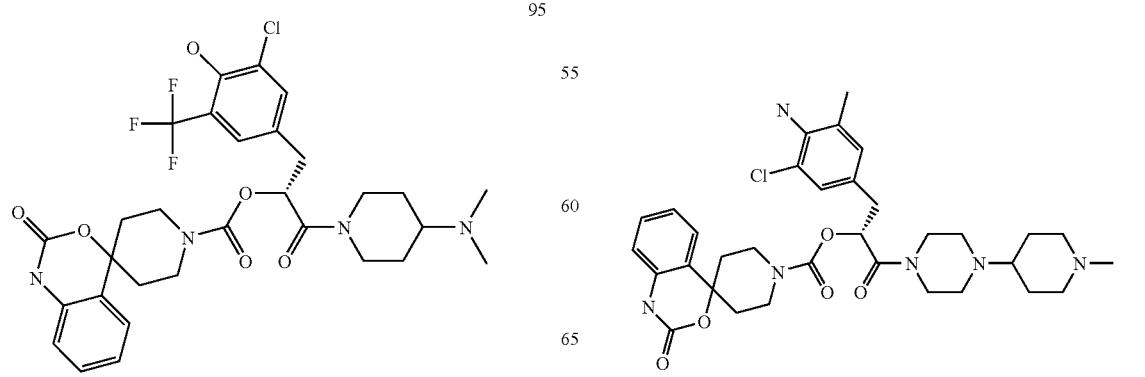
99

-continued
100
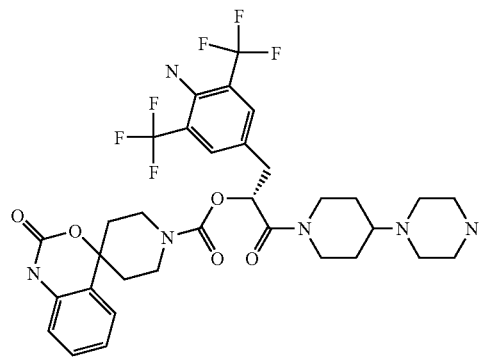
101
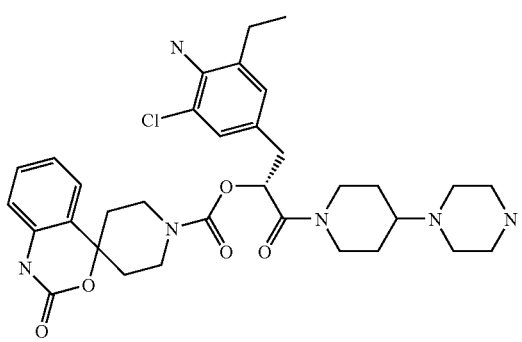
102
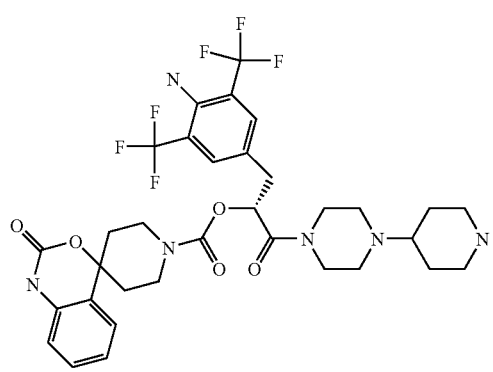
103
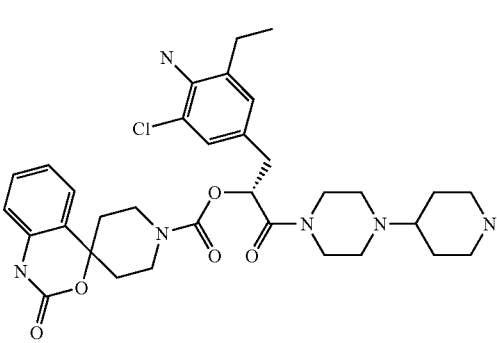
-continued
104
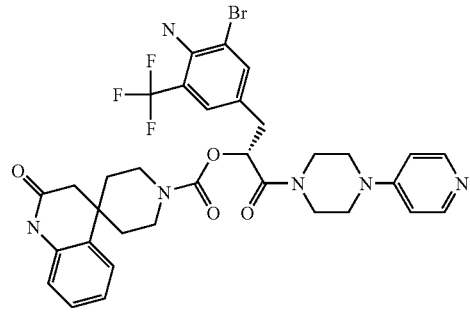
105
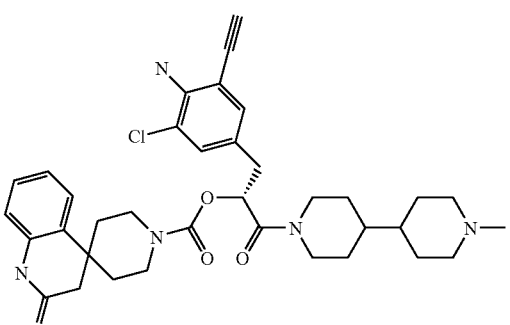
106
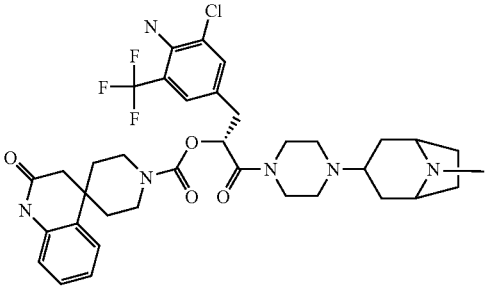
107
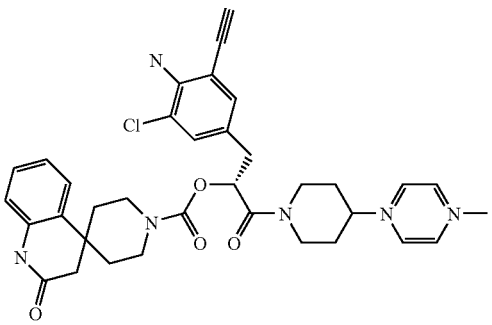
108
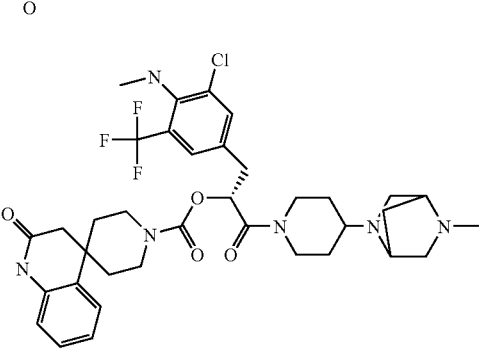

-continued
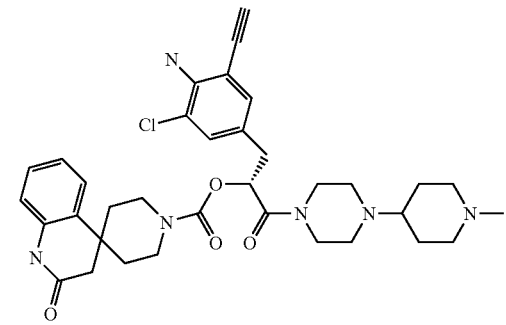
109
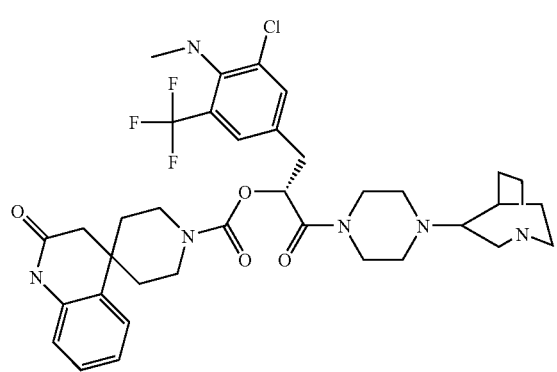
110
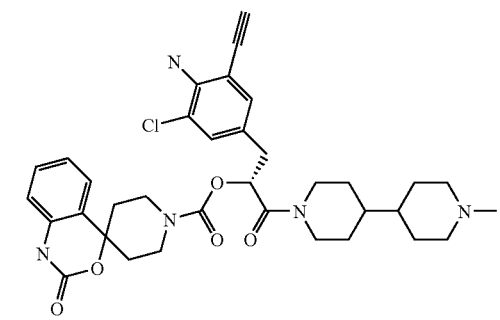
111
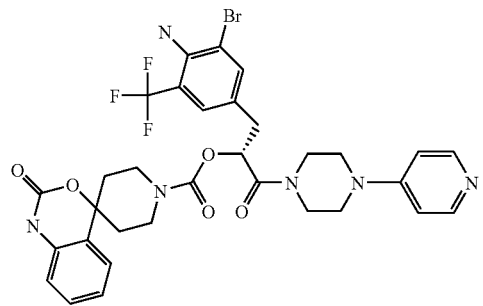
112
-continued
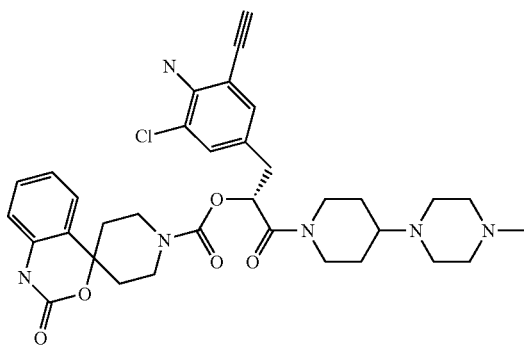
113
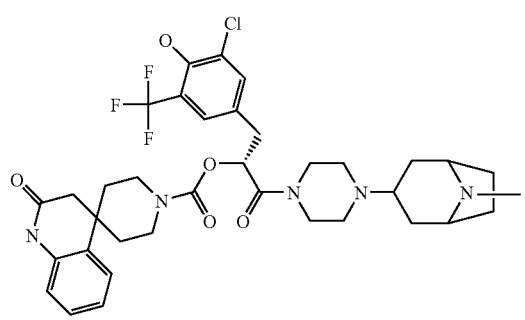
114
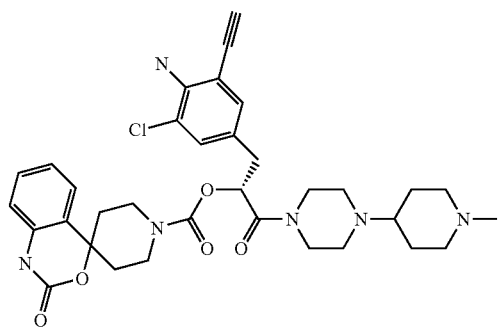
115
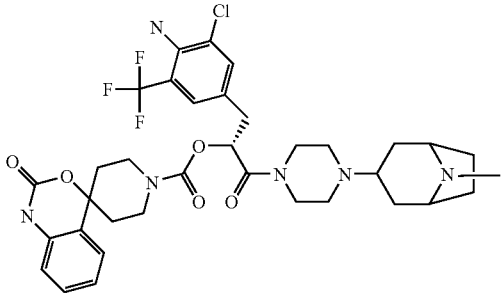
116
117

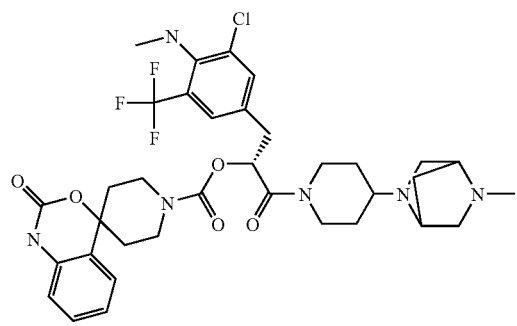
118
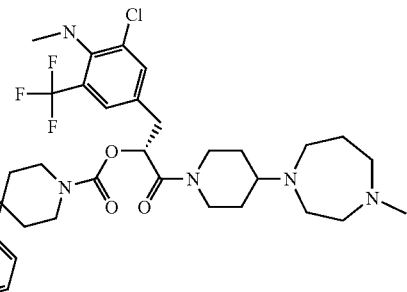
122
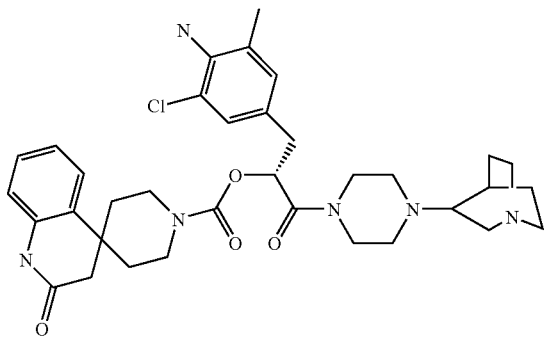
119
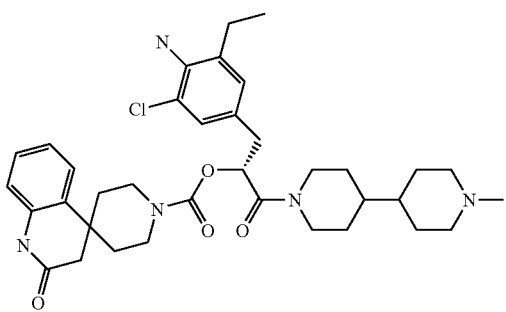
123
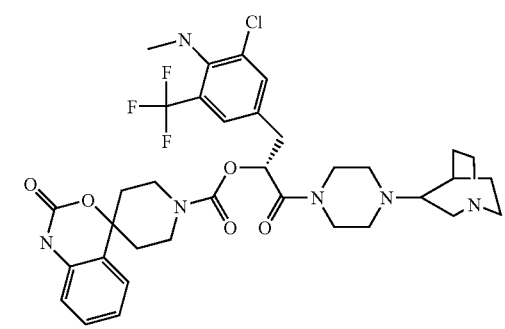
120
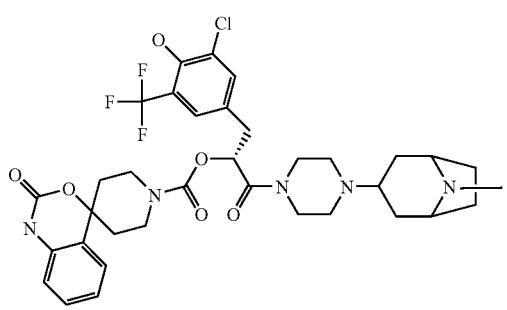
124
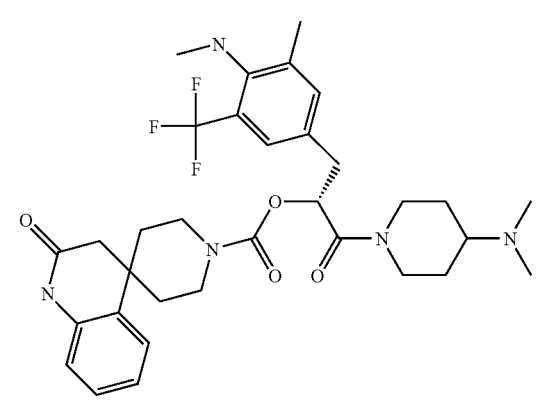
121
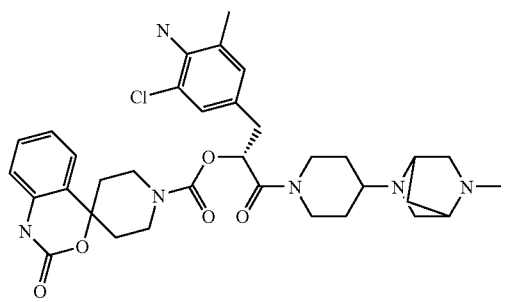
125
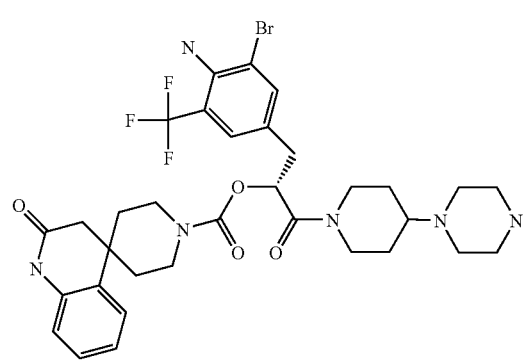
126

-continued

-continued
136
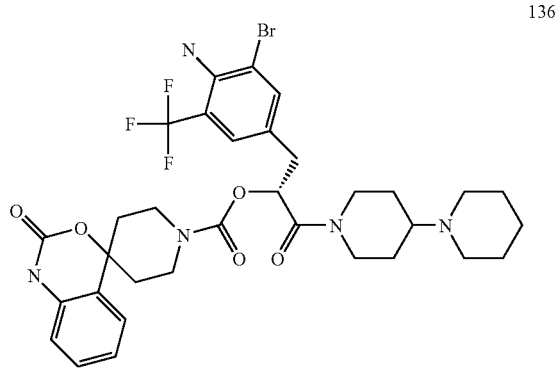
137
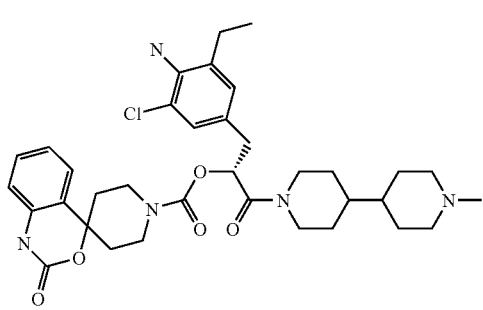
138
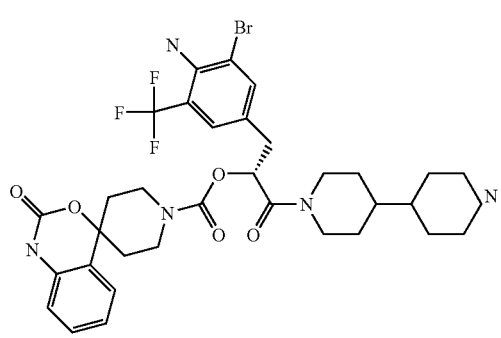
139
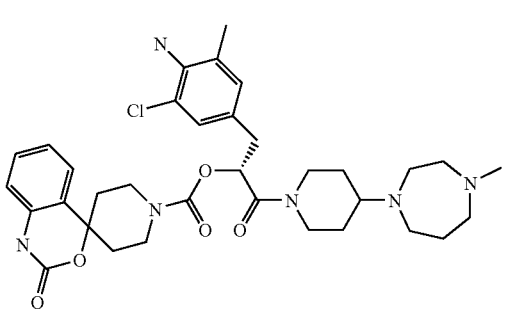
140
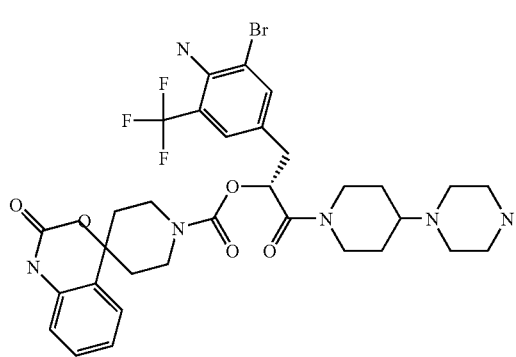
-continued
141
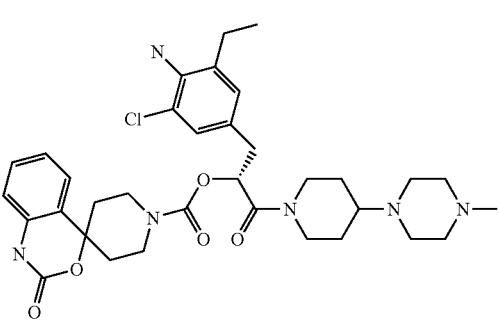
142
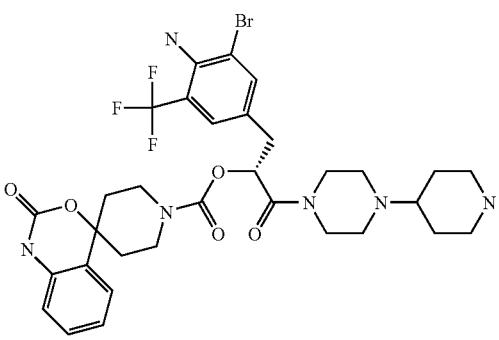
143
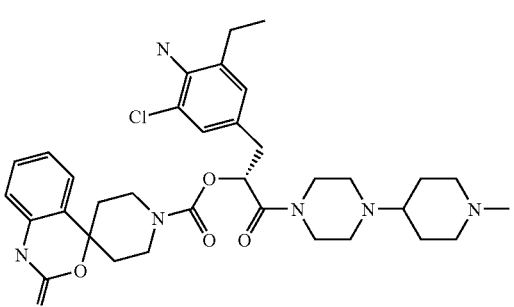
144
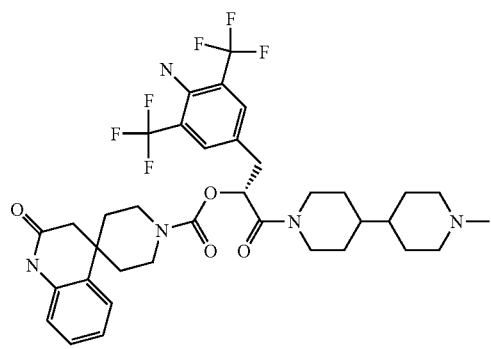
145
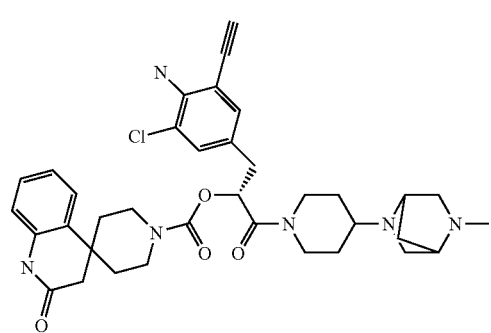

146 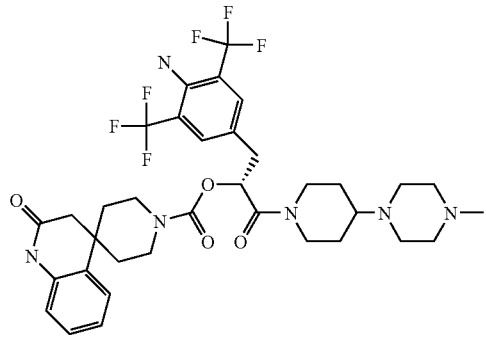
147 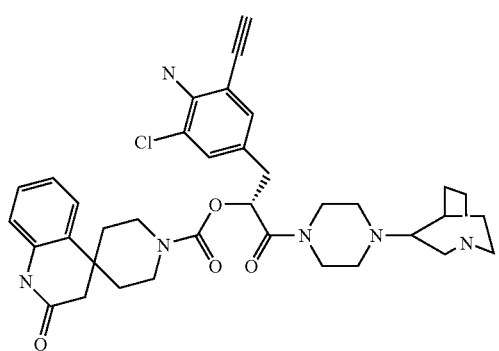
148 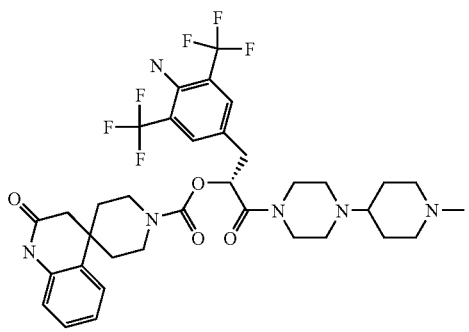
149 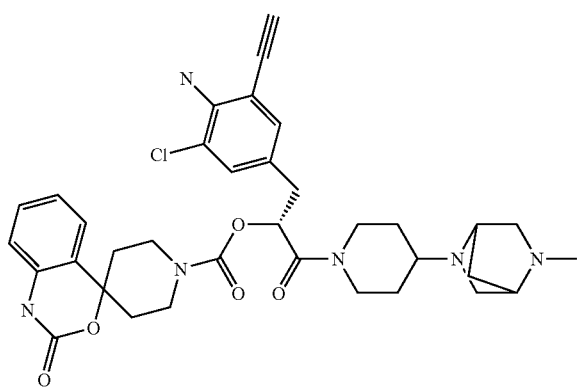
150 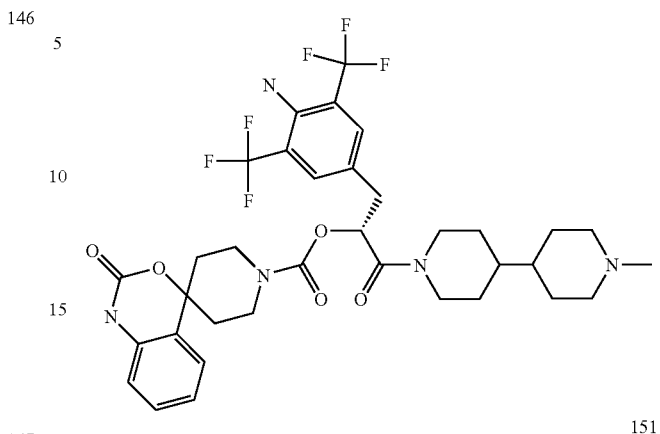
151 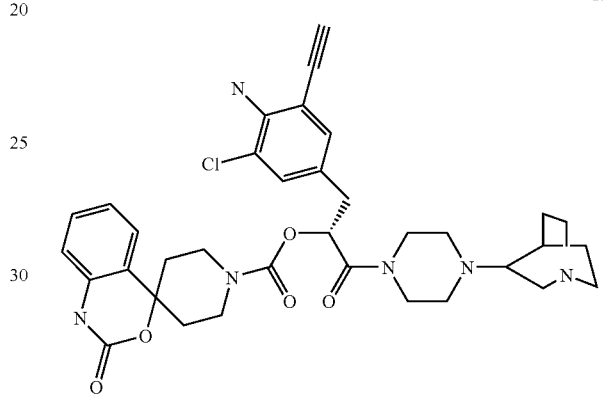
152 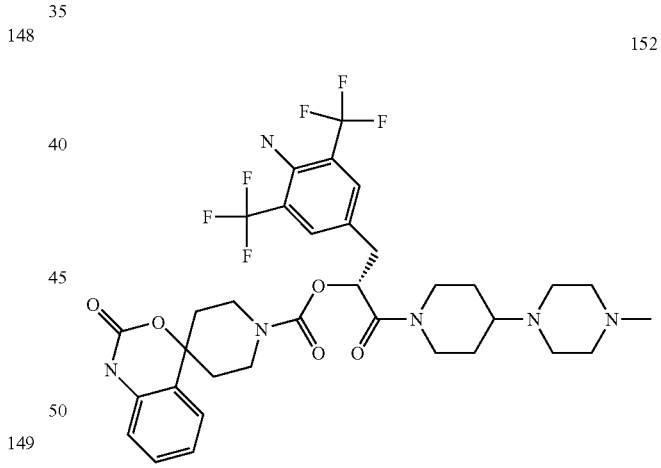
153 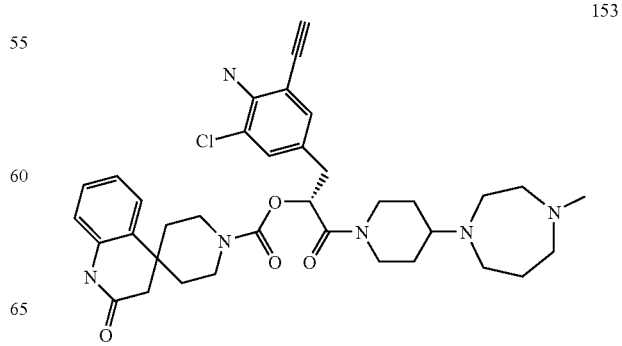

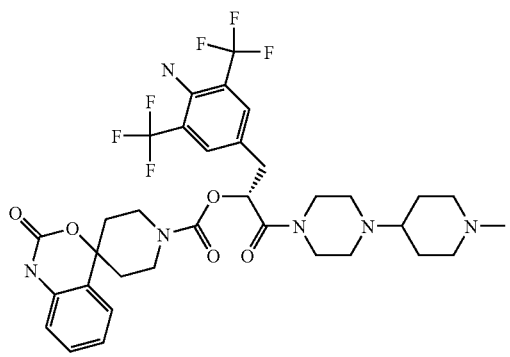
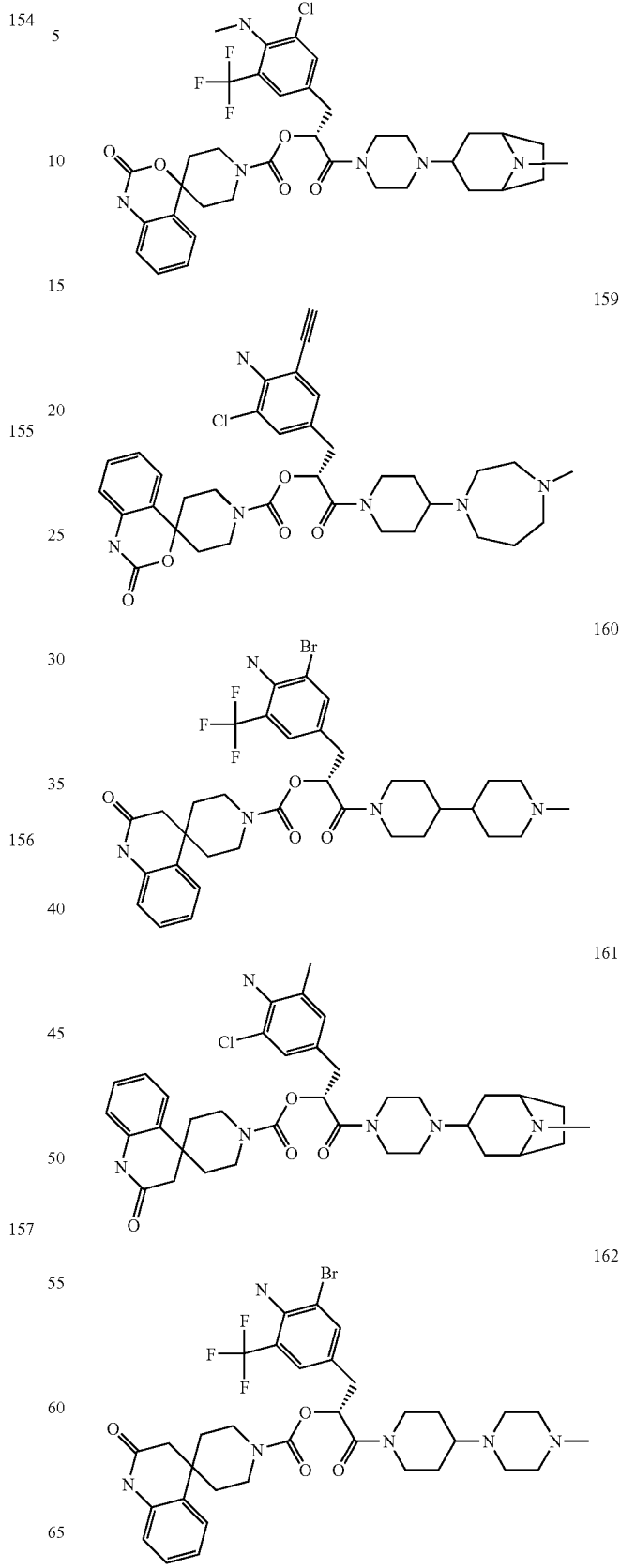

163
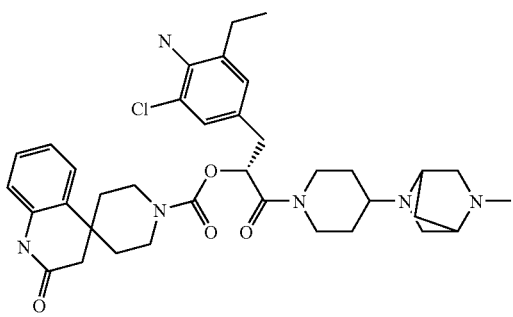
164
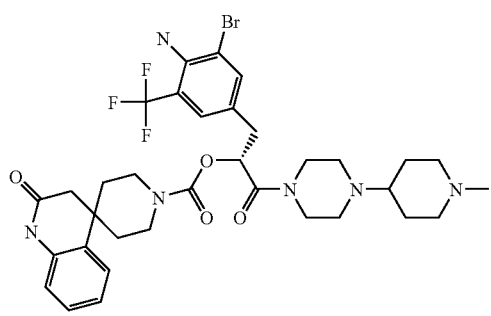
165
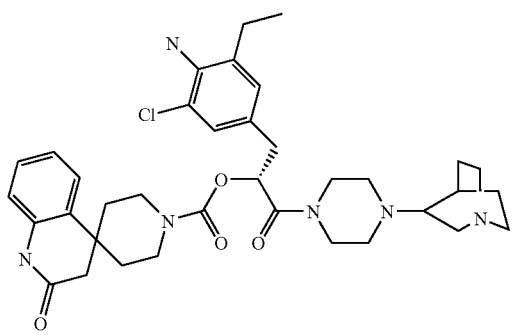
166
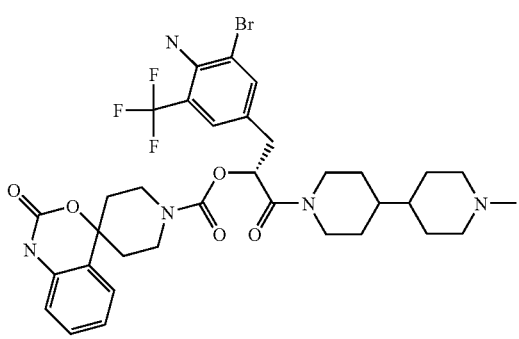
167
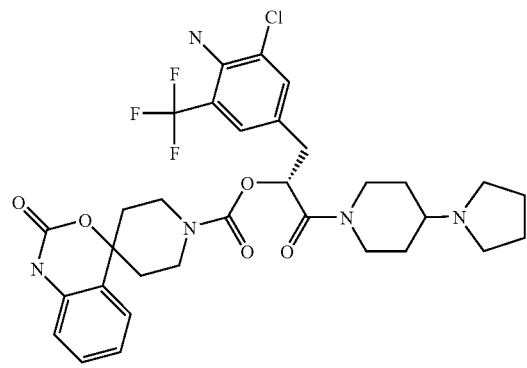
168
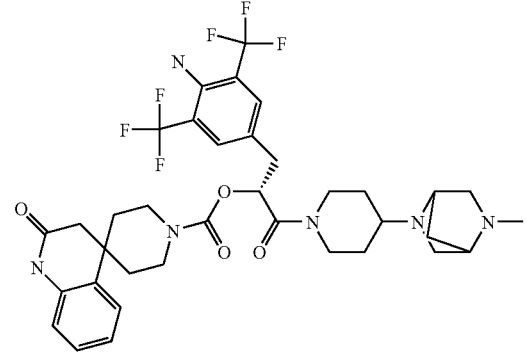
169
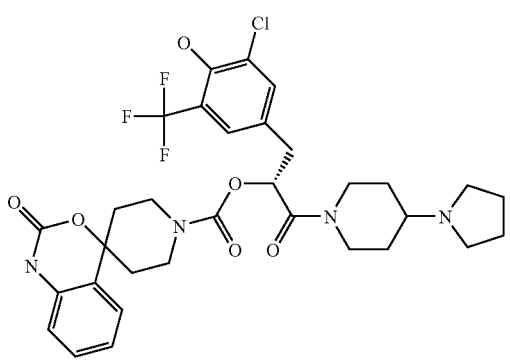
170
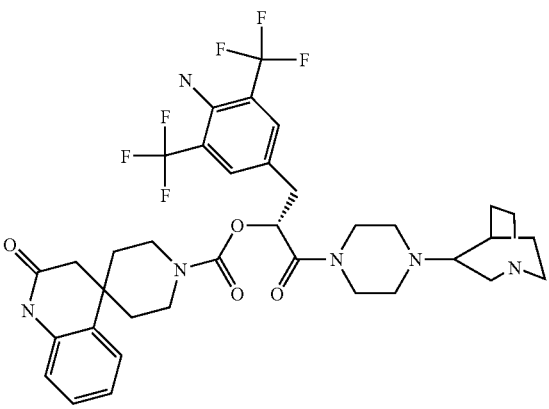

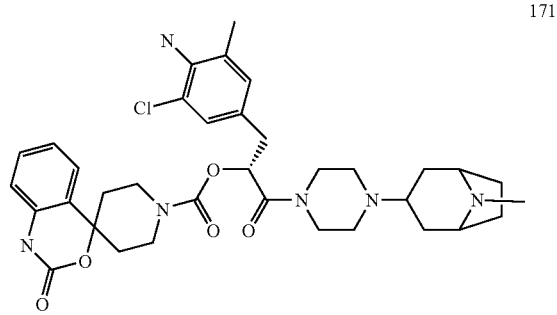
171
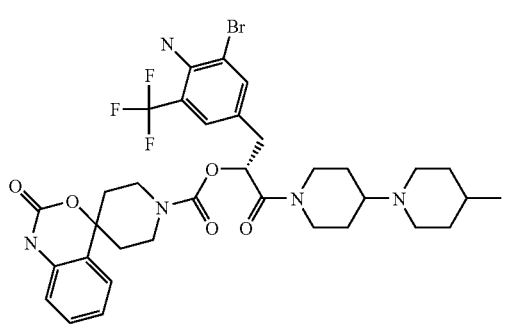
172
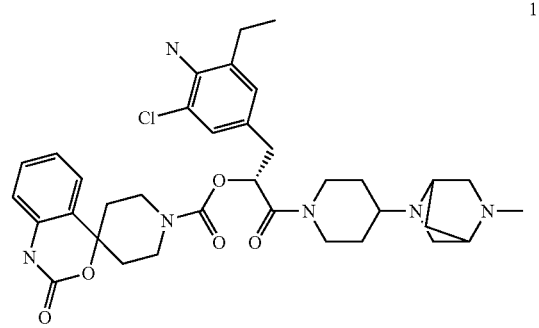
173
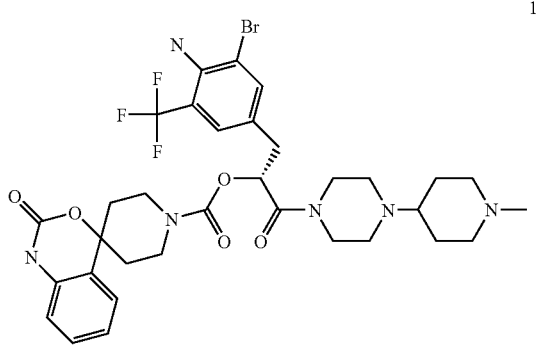
174
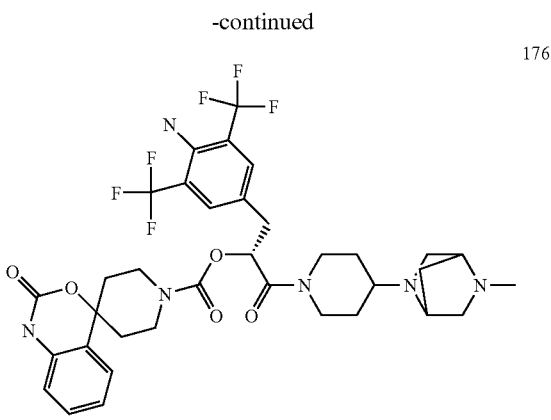
176
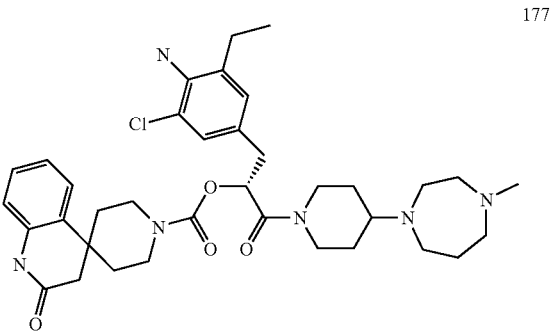
177
175
178
179

-continued
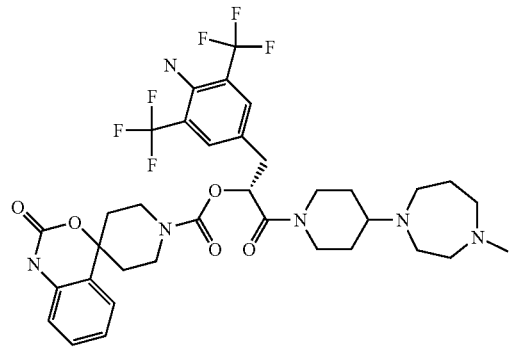
180
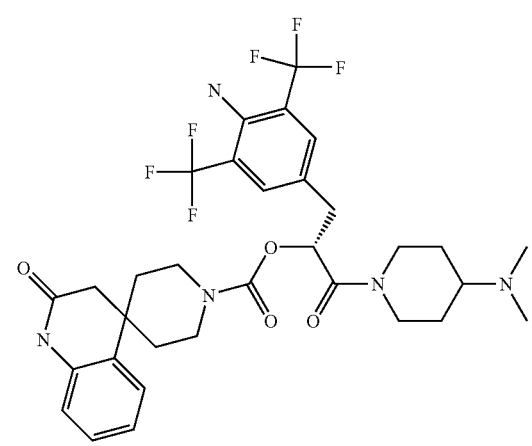
181
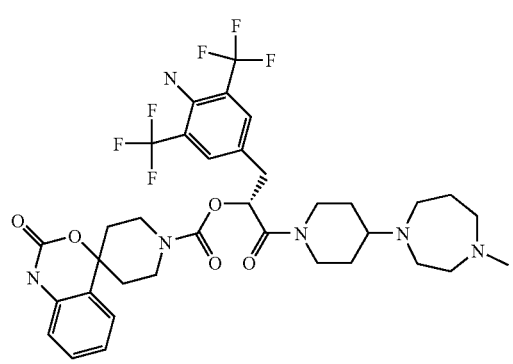
182
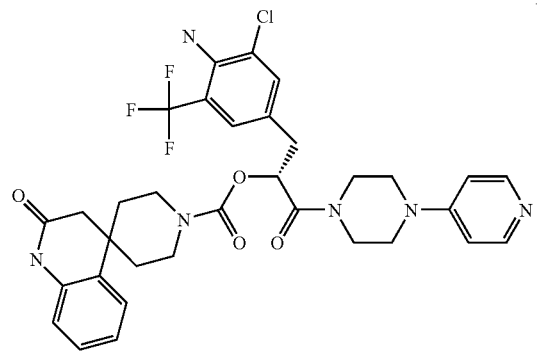
183
-continued
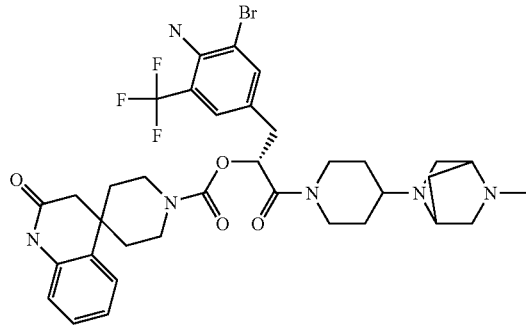
184
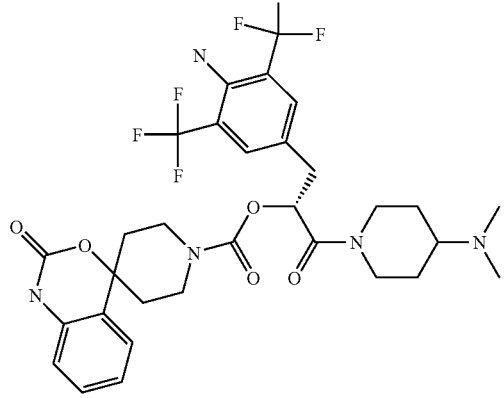
185
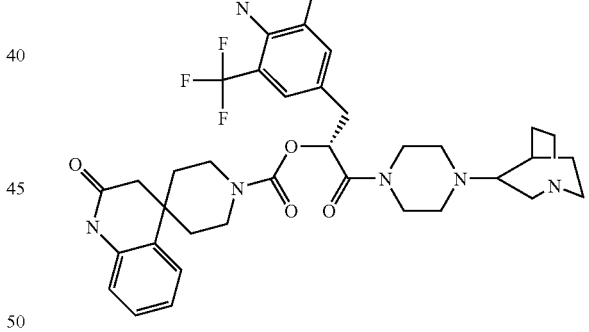
186
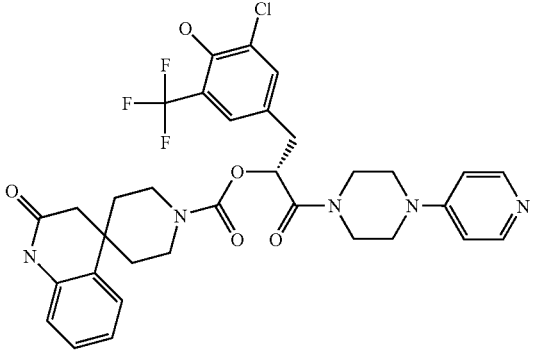
187

-continued
188
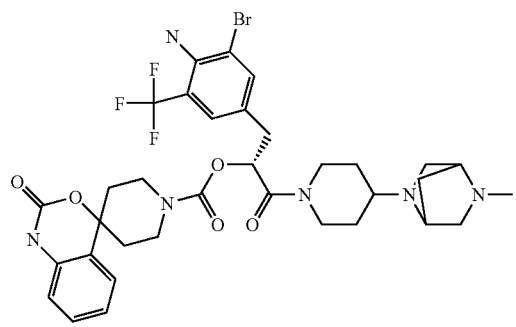
189
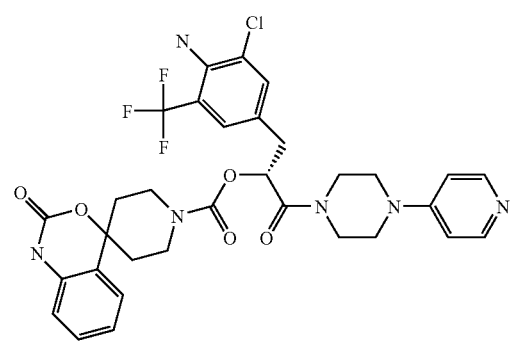
190
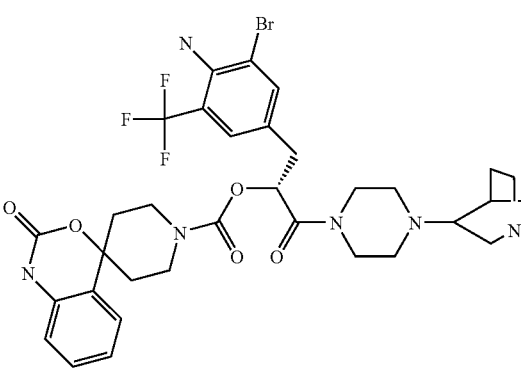
191
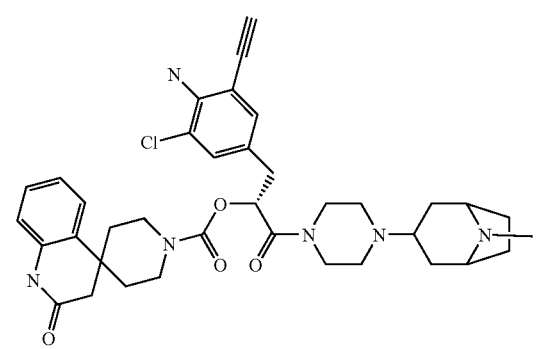
-continued
192
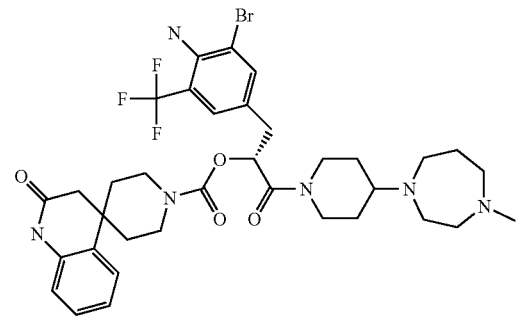
193
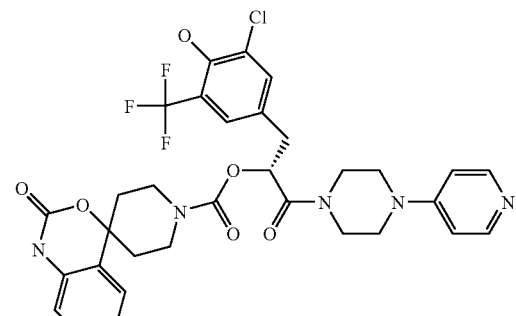
194
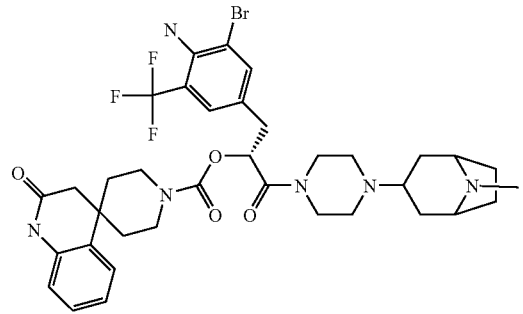
195
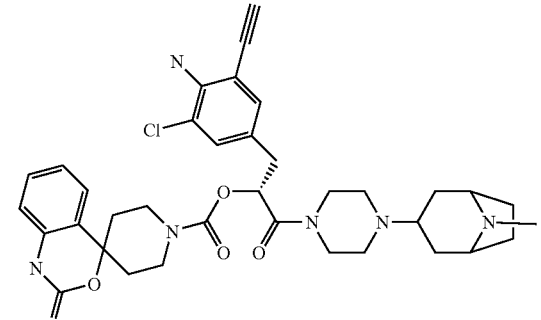
196
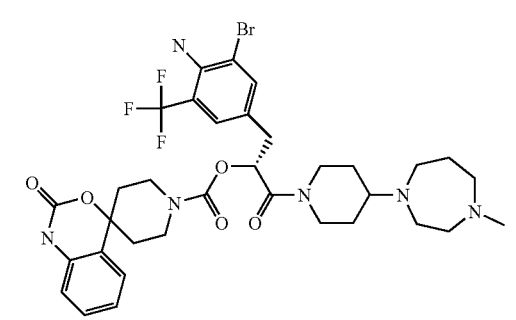

-continued

205
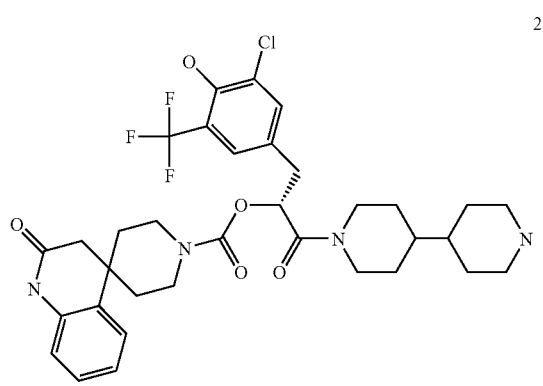
206
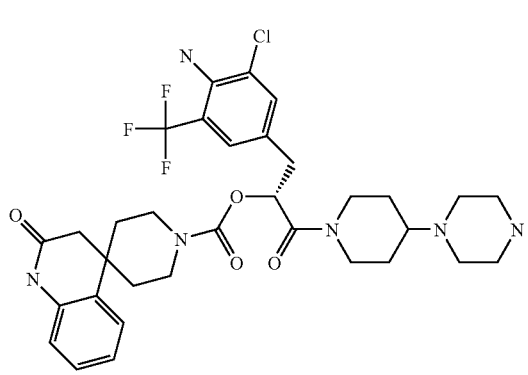
207
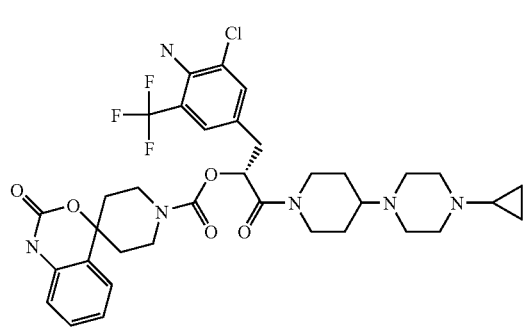
208
209
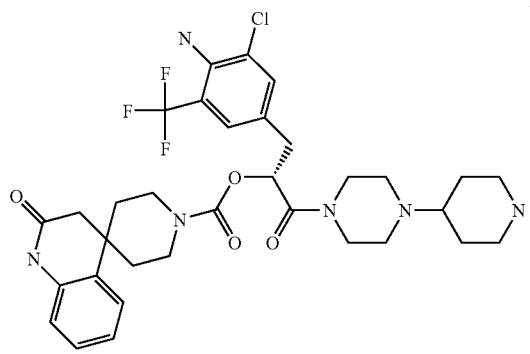
210
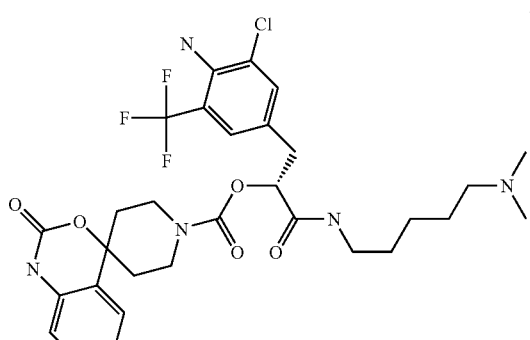
211
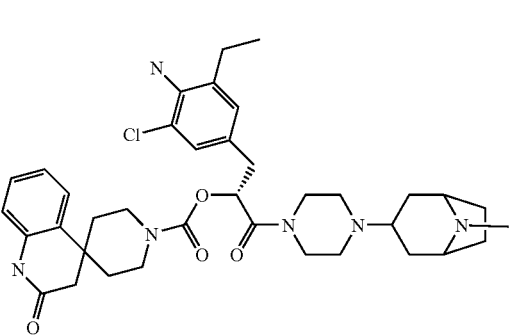
212
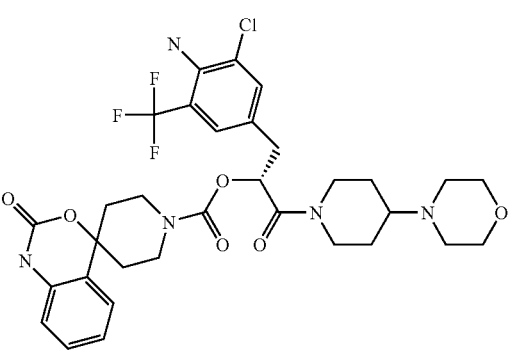

-continued
221
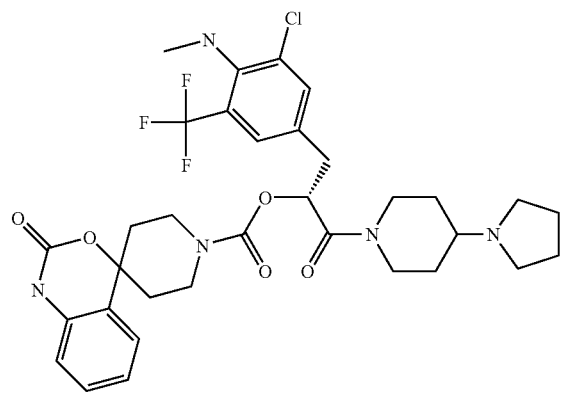
222
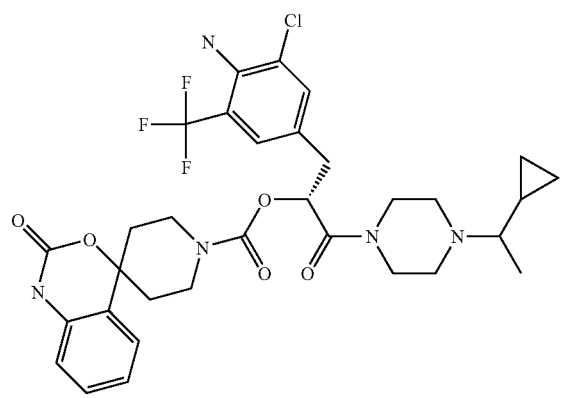
223
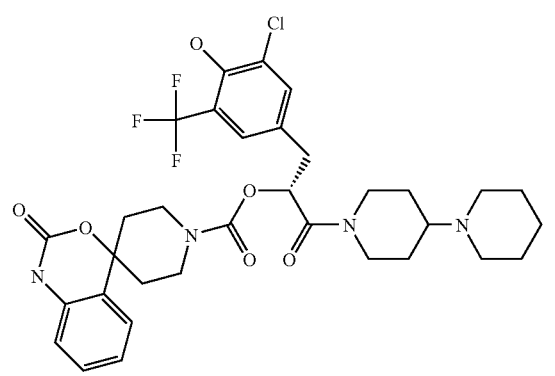
224
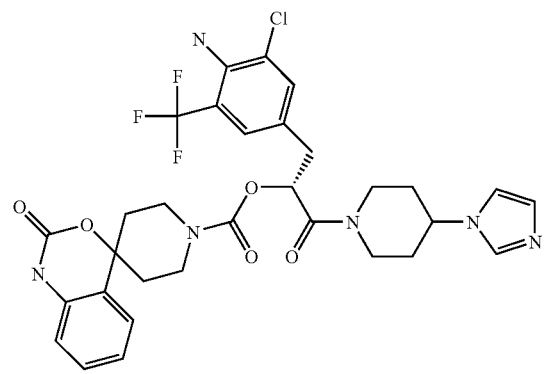
-continued
225
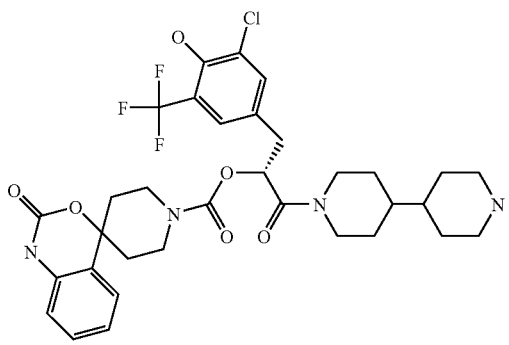
226
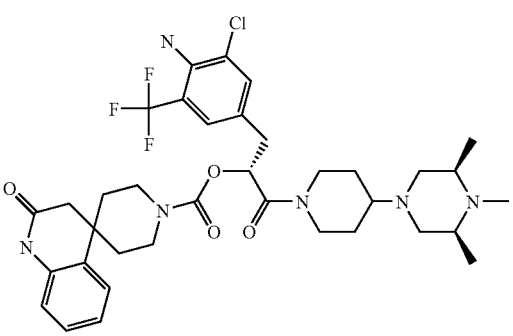
227
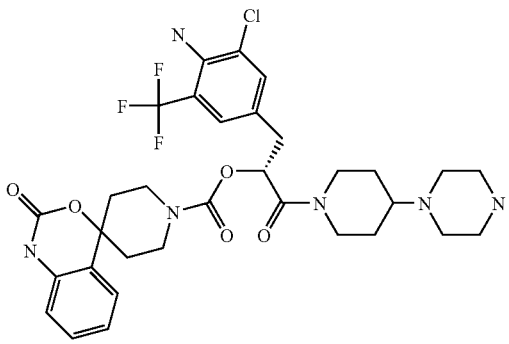
228
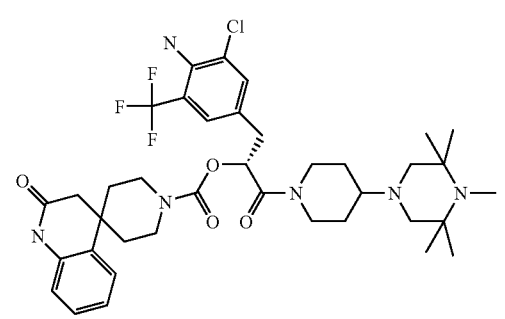

229
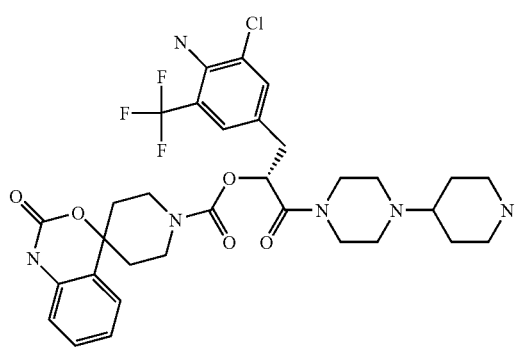
233
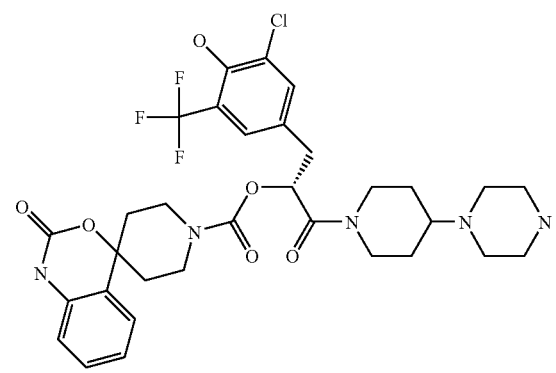
230
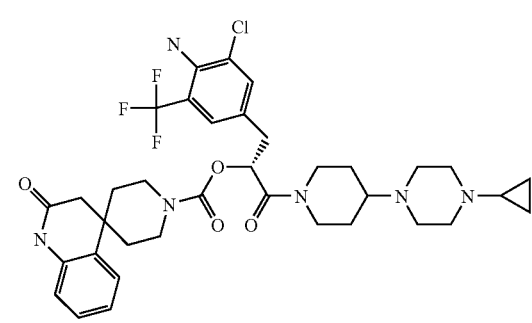
234
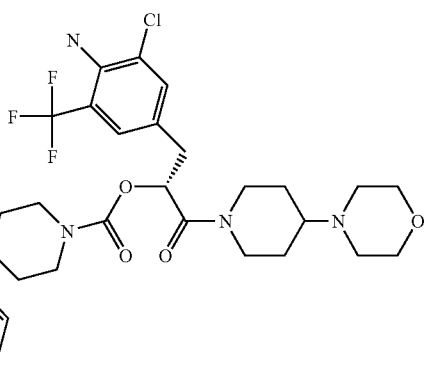
231
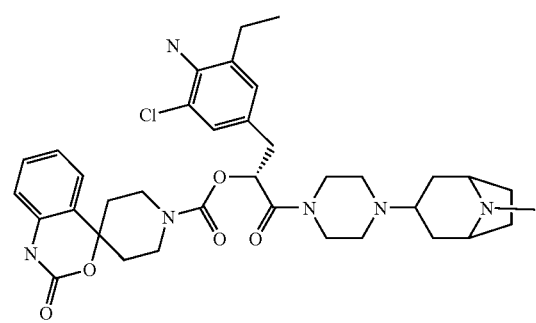
235
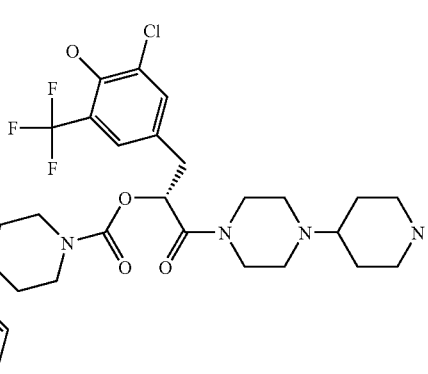
232
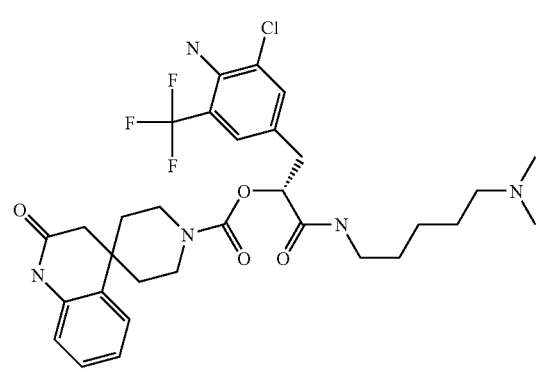
236
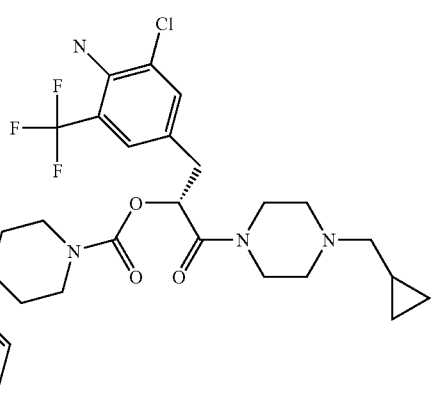

-continued
237
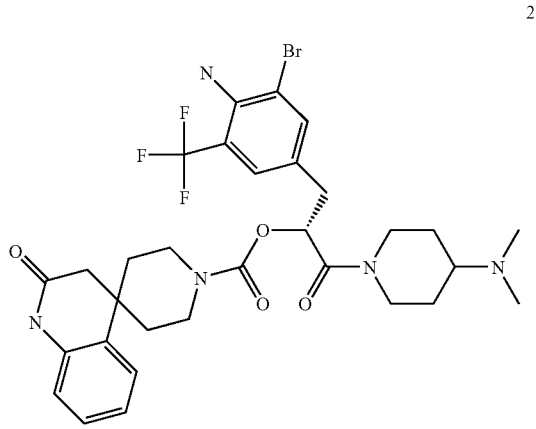
238
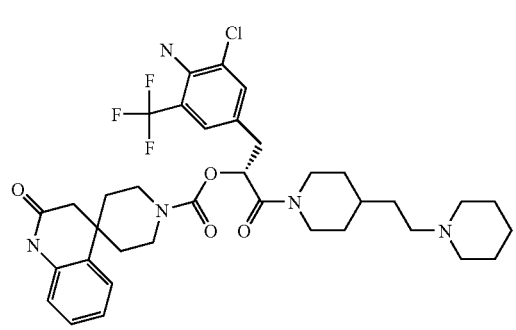
239
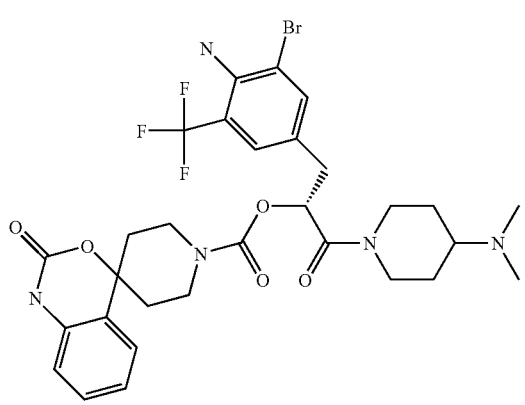
240
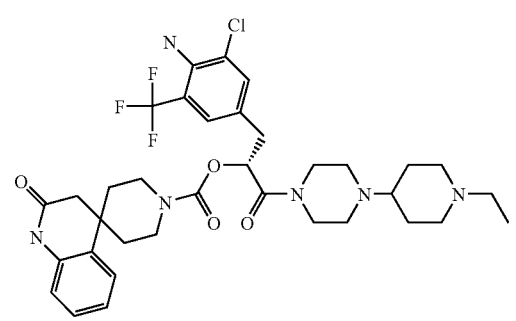
-continued
241
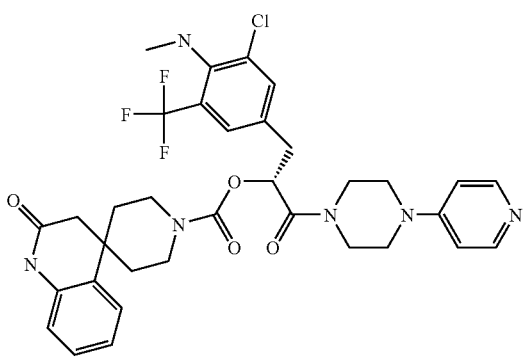
242
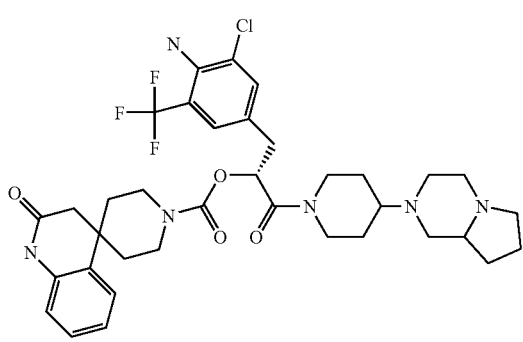
243
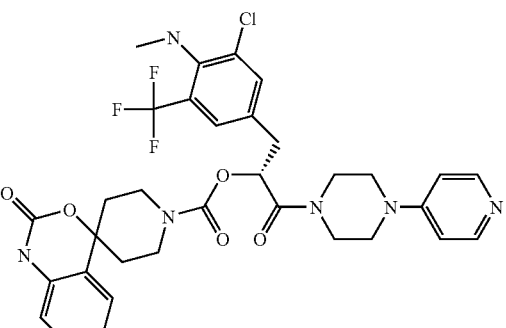
244
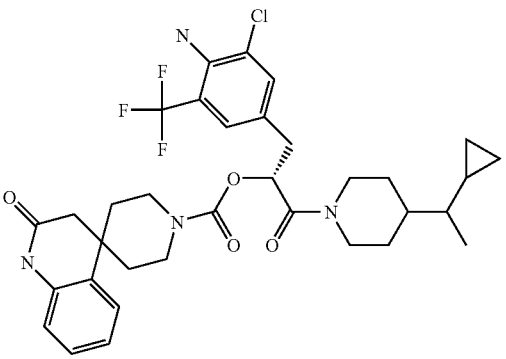

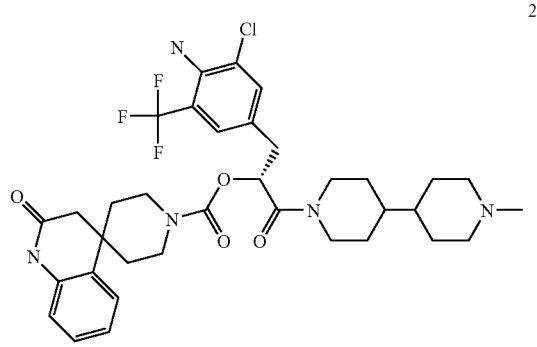
245
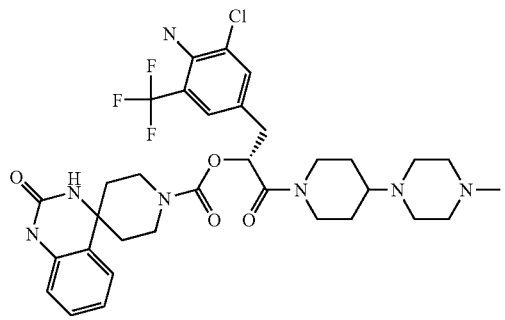
249
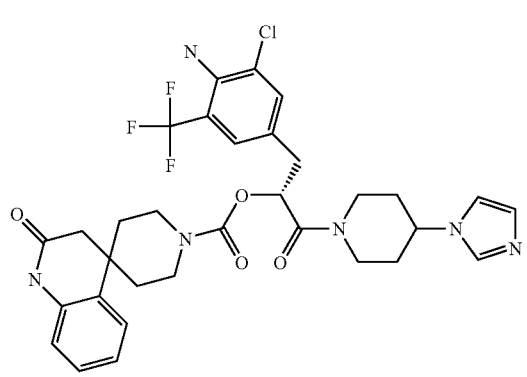
246
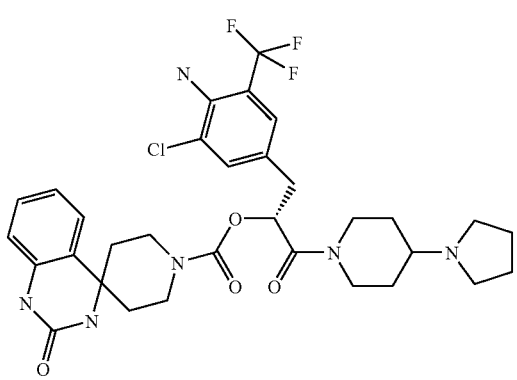
250
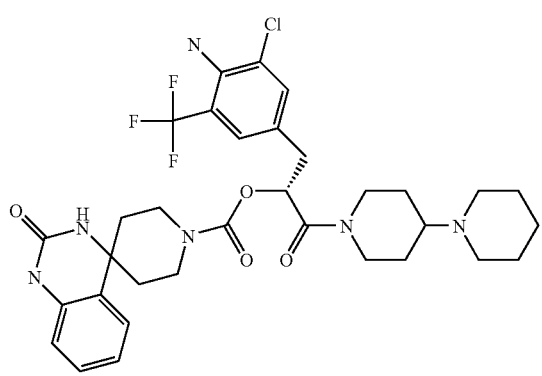
247
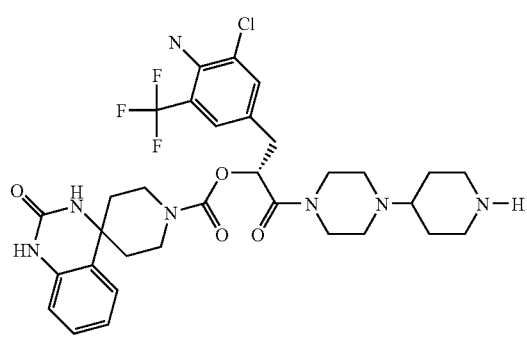
251
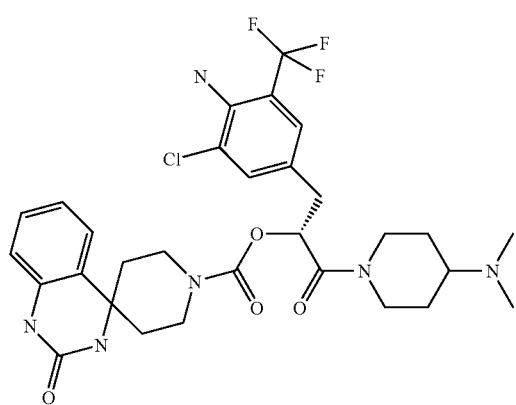
248
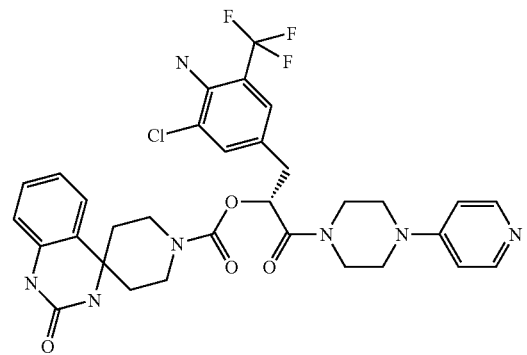
252

253

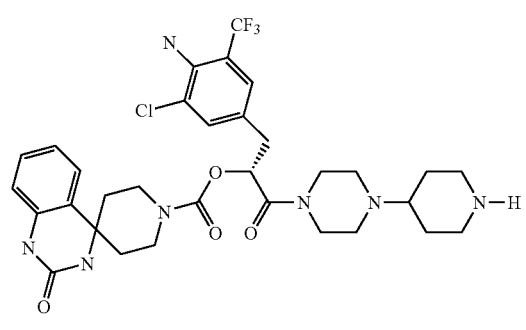

254

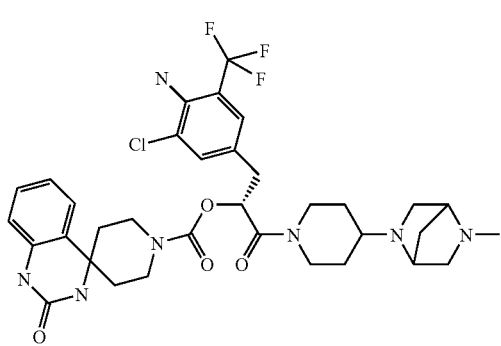

255

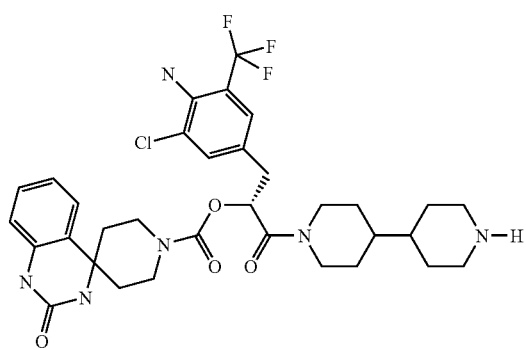

256

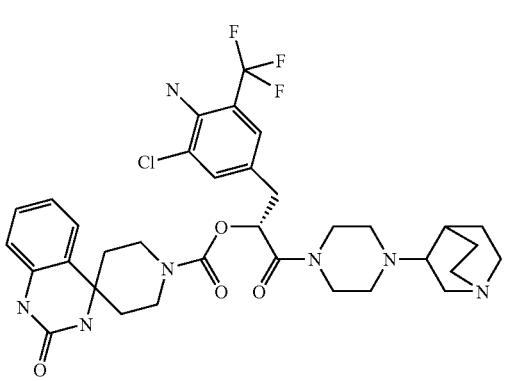

257

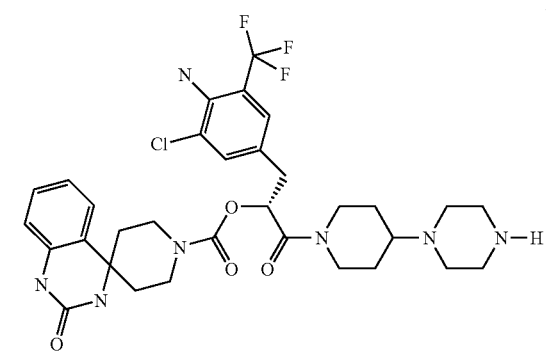

258 the tautomers, the diastereomers, the enantiomers, the hydrates thereof, the mixtures thereof and the salts thereof as well as the hydrates of the salts.

The compounds of general formula (I) are prepared by methods known in principle. The following methods have proved particularly useful for preparing the compounds of general formula (I) according to the invention:

(a) In order to prepare compounds of general formula

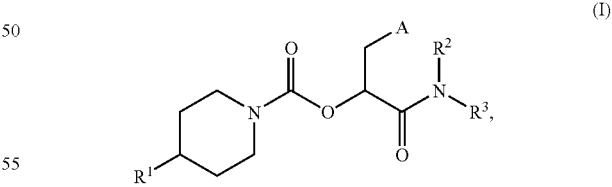

(I)

wherein A and $R^1$ to $R^3$ are as hereinbefore defined:

reacting a piperidine of general formula

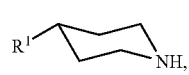

(II)

wherein $R^1$ is as hereinbefore defined, with a carbonic acid derivative of general formula

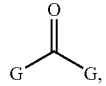

(III)

wherein G denotes a nucleofugic group which may be identical or different, preferably the chlorine atom, the p-nitrophenoxy or trichloromethoxy group, and with a compound of general formula

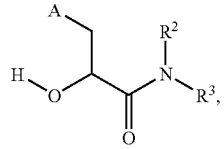

(IV)

wherein A, $R^2$ and $R^3$ are as hereinbefore defined, with the proviso that $R^2$ and $R^3$ do not contain any other free, unprotected, primary or secondary aliphatic amino function.

The reactions which are theoretically two-step reactions are usually carried out as one-pot processes, preferably by reacting one of the two components (II) or (IV) with equimolar quantities of the carbonic acid derivative of general formula (III) in a suitable solvent at lower temperature in the first stage, then adding at least equimolar amounts of the other component (II) or (IV) and finishing the reaction at elevated temperature. The reactions with bis-(trichloromethyl)-carbonate are preferably carried out in the presence of at least 2 equivalents (based on bis-(trichloromethyl)-carbonate) of a tertiary base, e.g. triethylamine, N-ethyl-diisopropylamine, pyridine, 1,5-diazabicyclo[4,3,0]non-5-ene, 1,4-diazabicyclo[2,2,2]octane or 1,8-diazabicyclo[5,4,0]undec-7-ene. Examples of solvents, which should be anhydrous, include tetrahydrofuran, dioxane, dimethyl formamide, dimethylacetamide, N-methyl-2-pyrrolidone, 1,3-dimethyl-2-imidazolidinone or acetonitrile; if bis-(trichloromethyl)-carbonate is used as the carbonyl component anhydrous chlorohydrocarbons such as dichloromethane, 1,2-dichloroethane or trichloroethylene are preferred. The reaction temperatures for the first reaction step are between −30 and +25° C., preferably −5 and +10° C., for the second reaction step they are between +15° C. and the boiling temperature of the solvent used, preferably between +20° C. and +70° C. (cf. also: H. A. Staab and W. Rohr, "Synthesen mit heterocyclischen Amiden (Azoliden)", Neuere Methoden der Präparativen Organischen Chemie, Vol. V, p. 53-93, Verlag Chemie, Weinheim/Bergstr., 1967; P. Majer and R. S. Randad, J. Org. Chem. 59, 1937-1938 (1994); K. Takeda, Y. Akagi, A. Saiki, T. Sukahara and H. Ogura, Tetrahedron Letters 24 (42), 4569-4572 (1983); S. R. Sandler and W. Karo in "Organic Functional Group Preparations", Vol. II, p. 223-245, Academis Press, New York 1971).

(b) In order to prepare compounds of general formula

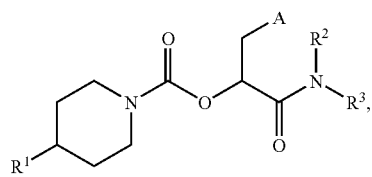

(I)

wherein A and $R^1$ to $R^3$ are as hereinbefore defined:

coupling a carboxylic acid of general formula

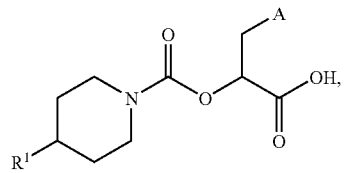

(V)

wherein A and $R^1$ are as hereinbefore defined, with an amine of general formula $HNR^2R^3$, wherein $R^2$ and $R^3$ are as hereinbefore defined, with the proviso that they do not contain any other free unprotected primary or secondary aliphatic amino function.

Any primary or secondary amino function additionally present in the group $-NR^2R^3$ is in each case provided with a suitable protective group.

The coupling is preferably carried out using methods known from peptide chemistry (cf. e.g. Houben-Weyl, Methoden der Organischen Chemie, Vol. 15/2), for example using carbodiimides such as e.g. dicyclohexylcarbodiimide (DCC), diisopropyl carbodiimide (DIC) or ethyl-(3-dimethylaminopropyl)-carbodiimide, O-(1H-benzotriazol-1-yl)-N,N-N',N'-tetramethyluronium hexafluorophosphate (HBTU) or tetrafluoroborate (TBTU) or 1H-benzotriazol-1-yl-oxy-tris-(dimethylamino)-phosphonium hexafluorophosphate (BOP). By adding 1-hydroxybenzotriazole (HOBt) or 3-hydroxy-4-oxo-3,4-dihydro-1,2,3-benzotriazine (HOObt) the reaction speed can be increased. The couplings are normally carried out with equimolar amounts of the coupling components as well as the coupling reagent in solvents such as dichloromethane, tetrahydrofuran, acetonitrile, dimethyl formamide (DMF), dimethyl acetamide (DMA), N-methylpyrrolidone (NMP) or mixtures thereof and at temperatures between −30 and +30° C., preferably −20 and +25° C. If necessary, N-ethyl-diisopropylamine (Hünig base) is preferably used as an additional auxiliary base.

The so-called anhydride process is used as a further coupling method for synthesising compounds of general formula (I) (cf. also: M. Bodanszky, "Peptide Chemistry", Springer-Verlag 1988, p. 58-59; M. Bodanszky, "Principles of Peptide Synthesis", Springer-Verlag 1984, p. 21-27). The Vaughan variant of the mixed anhydride process is preferred (J. R. Vaughan Jr., J. Amer. Chem.Soc. 73, 3547 (1951)), in which the mixed anhydride is obtained from the carboxylic acid of general formula (V) which is to be coupled and monoisobutyl carbonate, using isobutyl chlorocarbonate in the presence of bases such as 4-methylmorpholine or 4-ethylmorpholine. The preparation of this mixed anhydride and the coupling with the amines of general formula $HNR^2R^3$ are carried out in a one-pot process, using the above-mentioned solvents and at temperatures between −20 and +25° C., preferably between 0° C. and +25° C.

(c) In order to prepare compounds of general formula

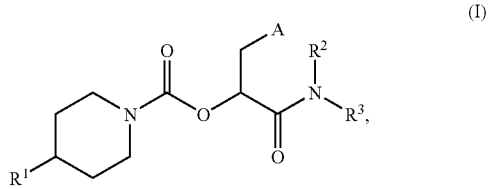

(I)

wherein A and R¹ to R³ are as hereinbefore defined:

coupling a compound of general formula

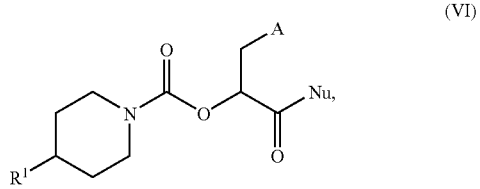

(VI)

wherein A and R¹ are as hereinbefore defined and Nu denotes a leaving group, for example a halogen atom, such as the chlorine, bromine or iodine atom, an alkyl-sulphonyloxy group with 1 to 10 carbon atoms in the alkyl moiety, a phenylsulphonyloxy or naphthylsulphonyloxy group optionally mono-, di- or trisubstituted by chlorine or bromine atoms, by methyl or nitro groups, while the substituents may be identical or different, a 1H-imidazol-1-yl, a 1H-pyrazol-1-yl optionally substituted by one or two methyl groups in the carbon skeleton, a 1H-1,2,4-triazol-1-yl, 1H-1,2,3-triazol-1-yl, 1H-1,2,3,4-tetrazol-1-yl, a vinyl, propargyl, p-nitrophenyl, 2,4-dinitrophenyl, trichlorophenyl, pentachlorophenyl, pentafluorophenyl, pyranyl or pyridinyl, a dimethylaminyloxy, 2(1H)-oxopyridin-1-yl-oxy, 2,5-dioxopyrrolidin-1-yloxy, phthalimidyloxy, 1H-benzo-triazol-1-yloxy or azide group, with an amine of general formula HNR²R³, wherein R² and R³ are as hereinbefore defined, with the proviso that no other free, unprotected, primary or secondary aliphatic amino function is present.

The reaction is carried out under Schotten-Baumann or Einhorn conditions, i.e. the components are reacted in the presence of at least one equivalent of an auxiliary base at temperatures between −50° C. and +120° C., preferably −10° C. and +30° C., and optionally in the presence of solvents. The auxiliary bases used are preferably alkali metal and alkaline earth metal hydroxides, e.g. sodium hydroxide, potassium hydroxide or barium hydroxide, alkali metal carbonates, e.g. sodium carbonate, potassium carbonate or caesium carbonate, alkali metal acetates, e.g. sodium or potassium acetate, as well as tertiary amines, e.g. pyridine, 2,4,6-trimethylpyridine, quinoline, triethylamine, N-ethyl-diisopropylamine, N-ethyl-dicyclohexylamine, 1,4-diazabi-cyclo[2,2,2]octane or 1,8-diazabicyclo[5,4,0]undec-7-ene, the solvents used may be, for example, dichloromethane, tetrahydrofuran, 1,4-dioxane, acetonitrile, dimethyl formamide, dimethyl acetamide, N-methyl-pyrrolidone or mixtures thereof; if alkali metal or alkaline earth metal hydroxides, alkali metal carbonates or acetates are used as the auxiliary bases, water may also be added to the reaction mixture as co-solvent.

The new compounds of general formula (I) according to the invention contain one or more chiral centres. If for example there are two chiral centres the compounds may occur in the form of two pairs of diastereomeric antipodes. The invention covers the individual isomers as well as the mixtures thereof.

The diastereomers may be separated on the basis of their different physico-chemical properties, e.g. by fractional crystallisation from suitable solvents, by high pressure liquid or column chromatography, using chiral or preferably non-chiral stationary phases.

Racemates covered by general formula (I) may be separated for example by HPLC on suitable chiral stationary phases (e.g. Chiral AGP, Chiralpak AD). Racemates which contain a basic function can also be separated via the diastereomeric, optically active salts which are produced on reacting with an optically active acid, for example (+) or (−)-tartaric acid, (+) or (−)-diacetyl tartaric acid, (+) or (−)-monomethyl tartrate or (+)-camphorsulphonic acid.

According to a conventional method of separating isomers, the racemate of a compound of general formula (I) is reacted with one of the above-mentioned optically active acids or bases in equimolar amounts in a solvent and the resulting crystalline, diastereomeric, optically active salts thereof are separated using their different solubilities. This reaction may be carried out in any type of solvent provided that it is sufficiently different in terms of the solubility of the salts. Preferably, methanol, ethanol or mixtures thereof, for example in a ratio by volume of 50:50, are used. Then each of the optically active salts is dissolved in water, carefully neutralised with a base such as sodium carbonate or potassium carbonate, or with a suitable acid, e.g. dilute hydrochloric acid or aqueous methanesulphonic acid, and in this way the corresponding free compound is obtained in the (+) or (−) form.

The (R) or (S) enantiomer alone or a mixture of two optically active diastereomeric compounds covered by general formula (I) may also be obtained by performing the syntheses described above with a suitable reaction component in the (R) or (S) configuration.

The starting compounds of general formula (II) may be obtained, if they are not already known from the literature, according to the methods described in International Patent Application WO 03/104236. The starting compounds of general formula (III) are commercially obtainable. Compounds of general formula (IV) may be obtained by methods familiar to the peptide chemist from hydroxycarboxylic acids and amines of general formula HNR²R³.

To prepare compounds of general formula (IV), the hydroxycarboxylic acids of general formula

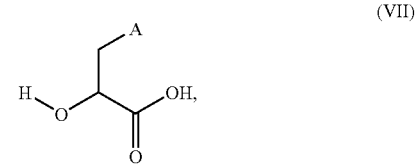

(VII)

wherein the group A is as hereinbefore defined, which are needed for the synthesis, may be obtained from compounds of general formula

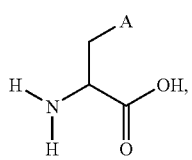
(VIII)

wherein A is as hereinbefore defined.

With the proviso that the group A does not contain an amino or methylamino group, by diazotising compounds of general formula (VIII) with a suitable diazotising reagent, preferably sodium nitrite in an acid medium, it is possible to obtain the compounds of general formula (VII). If enantiomerically pure compounds are used the corresponding enantiomerically pure hydroxycarboxylic acid compounds are obtained, the configuration being retained as the reaction proceeds.

Another method of obtaining compounds of general formula (VII) wherein the groups A are as hereinbefore defined comprises alkylating the compound

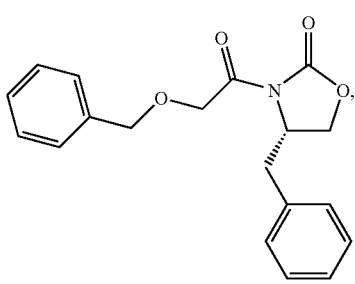
(IX)

with correspondingly substituted benzylchlorides, benzylbromides or benzyliodides of general formula

(X)

wherein A is as hereinbefore defined and X denotes a chlorine, bromine or iodine atom, analogously to methods known from the literature (Michael T. Crimmins, Kyle A. Emmitte and Jason D. Katz, Org. Lett. 2, 2165-2167 [2000]).

The diastereomeric products formed may then be separated using physicochemical methods, preferably chromatographic methods. The hydrolytic cleaving of the chiral auxiliary, coupling with amines of general formula $HNR^2R^3$ and cleaving of the benzyl protective group also provides a way of obtaining enantiomerically pure hydroxycarboxylic acid compounds of general formula (IV).

Compounds of general formula (VII) wherein the groups A are as hereinbefore defined may also be obtained by boiling down 2-acetylamino-3-phenyl-acrylic acids of general formula

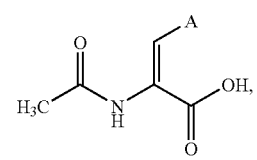
(XI)

using strong acids and subsequently reducing the 2-hydroxy-3-phenyl-acrylic acids formed.

The compounds of general formula (I) obtained may, if they contain suitable basic functions, be converted, particularly for pharmaceutical use, into their physiologically acceptable salts with inorganic or organic acids. Suitable acids include for example hydrochloric acid, hydrobromic acid, phosphoric acid, nitric acid, sulphuric acid, methanesulphonic acid, ethanesulphonic acid, benzenesulphonic acid, p-toluenesulphonic acid, acetic acid, fumaric acid, succinic acid, lactic acid, mandelic acid, malic acid, citric acid, tartaric acid or maleic acid.

The present invention relates to racemates if the compounds of general formula (I) have only one chiral element. However, the application also includes the individual diastereomeric pairs of antipodes or mixtures thereof which are obtained if there is more than one chiral element in the compounds of general formula (I), as well as the individual optically active enantiomers of which the above-mentioned racemates are made up.

Also included in the subject matter of this invention are the compounds according to the invention, including the salts thereof, in which one or more hydrogen atoms, for example one, two, three, four or five hydrogen atoms, are replaced by deuterium.

The new compounds of general formula (I) and the physiologically acceptable salts thereof have valuable pharmacological properties, based on their selective CGRP-antagonistic properties. The invention further relates to pharmaceutical compositions containing these compounds, their use and the preparation thereof.

The new compounds mentioned above and the physiologically acceptable salts thereof have CGRP-antagonistic properties and exhibit good affinities in CGRP receptor binding studies. The compounds display CGRP-antagonistic properties in the pharmacological test systems described hereinafter.

The following experiments were carried out to demonstrate the affinity of the above-mentioned compounds for human CGRP-receptors and their antagonistic properties:

A. Binding Studies with SK-N-MC Cells (Expressing the Human CGRP Receptor)

SK-N-MC cells are cultivated in "Dulbecco's modified Eagle medium". The medium is removed from confluent cultures. The cells are washed twice with PBS buffer (Gibco 041-04190 M), detached by the addition of PBS buffer mixed with 0.02% EDTA, and isolated by centrifuging. After resuspension in 20 ml of "Balanced Salts Solution" [BSS (in mM): NaCl 120, KCl 5.4, NaHCO$_3$ 16.2, MgSO$_4$ 0.8, NaHPO$_4$ 1.0, CaCl$_2$ 1.8, D-glucose 5.5, HEPES 30, pH 7.40] the cells are centrifuged twice at 100×g and resuspended in BSS. After the number of cells has been determined, the cells are homogenised using an Ultra-Turrax and centrifuged for 10 minutes at 3000×g. The supernatant is discarded and the pellet is recentrifuged in Tris buffer (10 mM Tris, 50 mM NaCl, 5 mM MgCl$_2$, 1 mM EDTA, pH 7.40) enriched with 1% bovine serum albumin and 0.1% bacitracin, and resuspended (1 ml/1000000 cells). The homogenised product is frozen at −80° C. The membrane preparations are stable for more than 6 weeks under these conditions.

After thawing, the homogenised product is diluted 1:10 with assay buffer (50 mM Tris, 150 mM NaCl, 5 mM $MgCl_2$, 1 mM EDTA, pH 7.40) and homogenised for 30 seconds with an Ultra-Turrax. 230 μl of the homogenised product are incubated for 180 minutes at ambient temperature with 50 pM $^{125}$I-iodotyrosyl-Calcitonin-Gene-Related Peptide (Amersham) and increasing concentrations of the test substances in a total volume of 250 μl. The incubation is ended by rapid filtration through GF/B-glass fibre filters treated with polyethyleneimine (0.1%) using a cell harvester. The protein-bound radioactivity is measured using a gamma counter. Non-specific binding is defined as the bound radioactivity in the presence of 1 μM human CGRP-alpha during incubation.

The concentration binding curves are analysed using computer-aided non-linear curve matching.

The compounds mentioned hereinbefore show $IC_{50}$ values ≦10000 nM in the test described.

B. CGRP Antagonism in SK-N-MC Cells

SK-N-MC cells (1 million cells) are washed twice with 250 μl incubation buffer (Hanks' HEPES, 1 mM 3-isobutyl-1-methylxanthine, 1% BSA, pH 7.4) and pre-incubated at 37° C. for 15 minutes. After the addition of CGRP (10 μl) as agonist in increasing concentrations ($10^{-11}$ to $10^{-6}$ M), or additionally the substance in 3 to 4 different concentrations, the mixture is incubated for another 15 minutes.

Intracellular cAMP is then extracted by the addition of 20 μl of 1 M HCl and centrifugation (2000×g, 4° C., for 15 minutes). The supernatants are frozen in liquid nitrogen and stored at −20° C.

The cAMP contents of the samples are determined by radioimmunoassay (Messrs. Amersham) and the $pA_2$ values of antagonistically acting substances are determined graphically.

The compounds of general formula (I) exhibit CGRP-antagonistic properties in the in vitro test model described, in a dosage range between $10^{-12}$ and $10^{-5}$ M.

In view of their pharmacological properties the compounds of general formula (I) and the salts thereof with physiologically acceptable acids are thus suitable for the acute and prophylactic treatment of headaches, particularly migraine or cluster headaches. Moreover, the compounds of general formula (I) also have a positive effect on the following diseases: non-insulin-dependent diabetes mellitus ("NIDDM"), complex regional pain syndrome (CRPS1), cardiovascular diseases, morphine tolerance, diarrhoea caused by clostridium toxin, skin diseases, particularly thermal and radiation-induced skin damage including sunburn, inflammatory diseases, e.g. inflammatory diseases of the joints (arthritis), neurogenic inflammation of the oral mucosa, inflammatory lung diseases, allergic rhinitis, asthma, diseases accompanied by excessive vasodilatation and resultant reduced blood supply to the tissues, e.g. shock and sepsis. In addition, the compounds according to the invention have a general pain-relieving effect.

The symptoms of menopausal hot flushes caused by vasodilatation and increased blood flow in oestrogen-deficient women and hormone-treated patients with prostate carcinoma are favourably affected by the CGRP-antagonists of the present application in a preventive and acute-therapeutic capacity, this therapeutic approach being distinguished from hormone replacement by the absence of side effects.

The dosage required to achieve a corresponding effect is conveniently 0.01 to 3 mg/kg of body weight, preferably 0.01 to 1 mg/kg of body weight, when administered intravenously or subcutaneously and 0.01 to 20 mg/kg of body weight, preferably 0.1 to 10 mg/kg of body weight when administered orally, and 0.01 to 10 mg/kg of body weight, preferably 0.1 to 10 mg/kg of body weight when administered nasally or by inhalation, 1 to 3× a day in each case.

If the treatment with CGRP antagonists and/or CGRP release inhibitors is given as a supplement to conventional hormone replacement, it is advisable to reduce the doses specified above, in which case the dosage may be from ⅕ of the lower limits mentioned above up to ¹/₁ of the upper limits specified.

The compounds prepared according to the invention may be administered either on their own or optionally in combination with other active substances for the treatment of migraine by intravenous, subcutaneous, intramuscular, intrarectal, intranasal route, by inhalation, transdermally or orally, while aerosol formulations are particularly suitable for inhalation. The combinations may be administered either simultaneously or sequentially.

Categories of active substance which may be used in the combination include e.g. angiotensin II receptor antagonists, α-agonists and α-antagonists, $5\text{-HT}_{1B/1D}$ agonists, AMPA antagonists, mild analgesics, antidepressants, antiemetics, anti-convulsants, antimuscarinics, β-blockers, calcium antagonists, corticosteroids, ergot alkaloids, histamine-H1 receptor antagonists, neurokinine antagonists, neuroleptics, non-steroidal antiinflammatories, NO-synthase inhibitors, prokinetics, selective serotonin reuptake inhibitors or other anti-migraine agents, which may be formulated together with one or more inert conventional carriers and/or diluents, e.g. with corn starch, lactose, glucose, microcrystalline cellulose, magnesium stearate, polyvinyl pyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, into conventional galenic preparations such as plain or coated tablets, capsules, powders, suspensions, solutions, metered dose aerosols or suppositories.

Thus other active substances which may be used for the combinations mentioned above include for example the non-steroidal antiinflammatories aceclofenac, acemetacin, acetylsalicylic acid, azathioprine, diclofenac, diflunisal, fenbufen, fenoprofen, flurbiprofen, ibuprofen, indometacin, ketoprofen, leflunomide, lornoxicam, mefenamic acid, naproxen, phenylbutazone, piroxicam, sulphasalazine, zomepirac or the pharmaceutically acceptable salts thereof as well as meloxicam and other selective COX2-inhibitors, such as for example rofecoxib and celecoxib.

It is also possible to use candesartan, eprosartan, irbesartan, losartan, olmesartan, tasosartan, telmisartan, valsartan, duloxetine, ergotamine, dihydroergotamine, metoclopramide, domperidone, diphenhydramine, cyclizine, promethazine, chlorpromazine, vigabatrin, timolol, isometheptene, pizotifen, botox, gabapentin, topiramate, riboflavin, montelukast, lisinopril, prochloroperazine, dexamethasone, flunarizine, dextropropoxyphene, meperidine, metoprolol, propranolol, nadolol, atenolol, clonidine, indoramin, carbamazepine, phenytoin, valproate, amitryptiline, lidocaine or diltiazem and other $5\text{-HT}_{1B/1D}$-agonists such as, for example, almotriptan, avitriptan, eletriptan, frovatriptan, naratriptan, rizatriptan, sumatriptan and zolmitriptan and the physiologically acceptable salts thereof.

The dosage of these active substances is expediently ⅕ of the lowest recommended dose to ⅓ of the normally recommended dose, i.e. for example 20 to 100 mg of sumatriptan.

The invention further relates to the use of the compounds according to the invention as valuable adjuvants for the production and purification (by affinity chromatography) of antibodies as well as in RIA and ELISA assays, after suitable radioactive labelling, for example by tritiation of suitable precursors, for example by catalytic hydrogenation with tritium or replacing halogen atoms with tritium, and as a diagnostic or analytical adjuvant in neurotransmitter research.

What is claimed is:

1. A compound of the formula

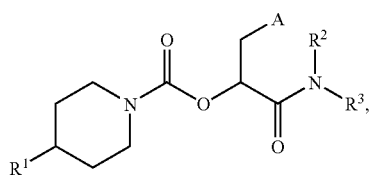
(I)

wherein

A denotes a group of formula

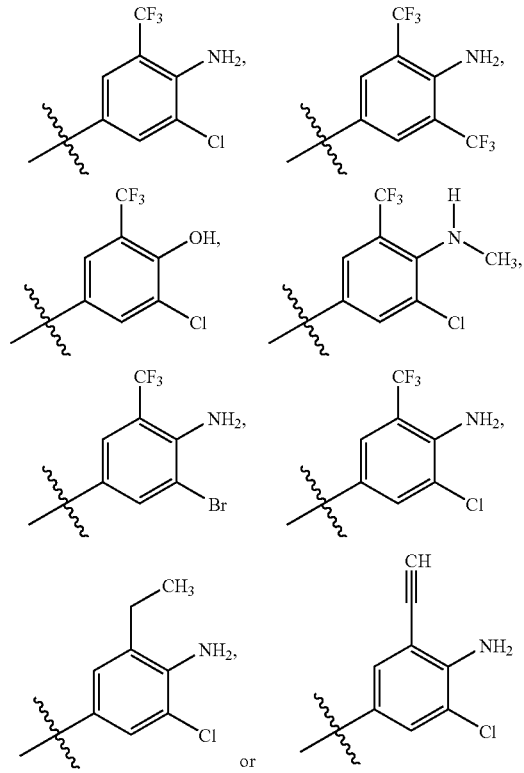
or the group

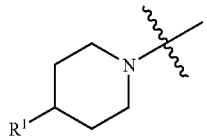

denotes a group of formula

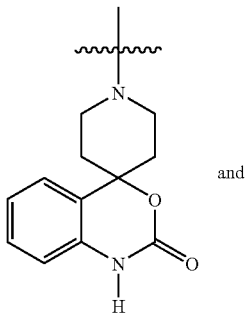
and

—$NR^2R^3$ denotes a group of formula

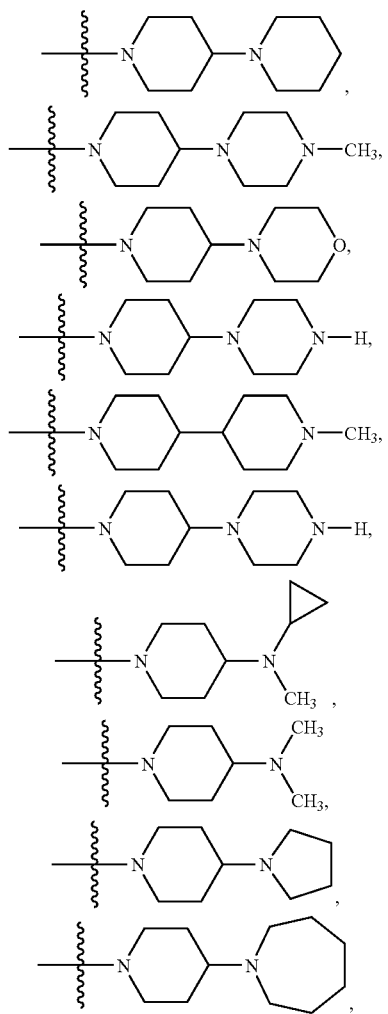

-continued

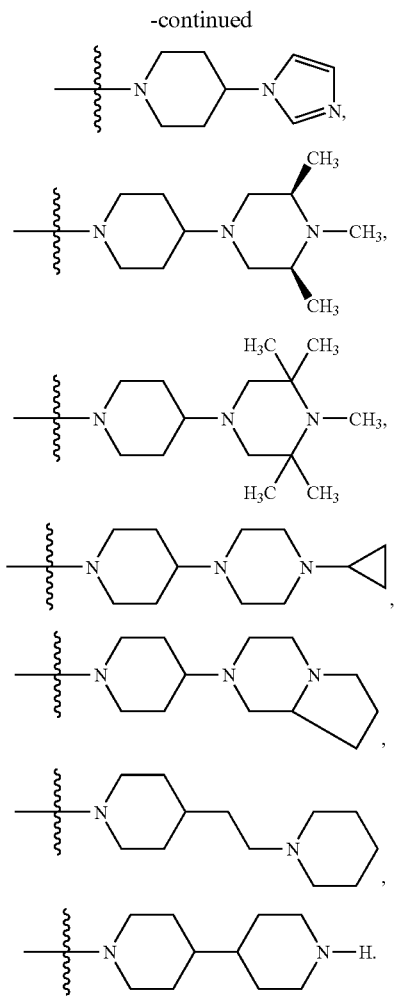

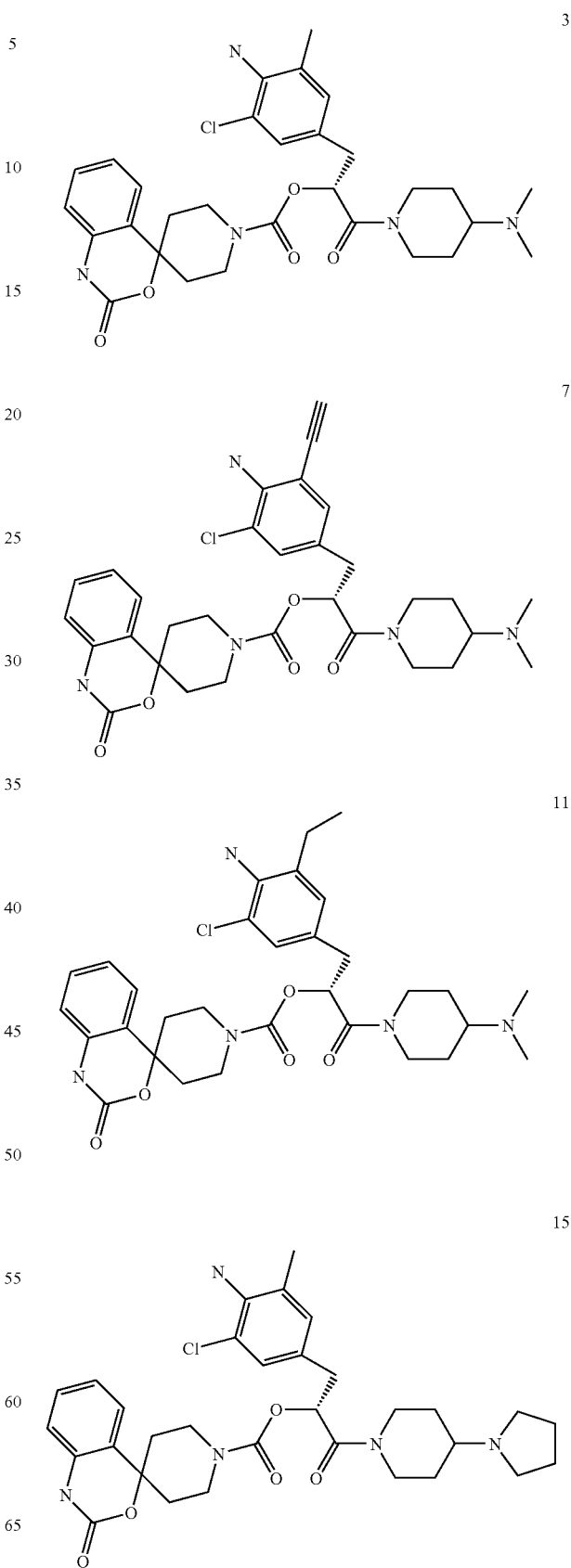

or a tautomer or salt thereof.

2. A compound of the formula (I) according to claim 1, selected from the group consisting of:

(e) (R)-1-(4-amino-3-chloro-5-trifluoromethyl-benzyl)-2-[4-(4-methyl-piperazin-1-yl) -piperidin-1-yl]-2-oxo-ethyl 1',2'-dihydro-2'-oxospiro-4H-3', 1-benzoxazin-4, 4'-piperidine-1-carboxylate, (f) (R)-1-(4-amino-3-chloro-5-trifluoromethyl-benzyl)-2-[4-(1-methyl-piperidin-4-yl) -piperazin-1-yl]-2-oxo-ethyl 1',2'-dihydro-2'-oxospiro-4H-3', 1-benzoxazin-4, 4'-piperidine-1-carboxylate, (g) (R)-1-(4-amino-3-chloro-5-trifluoromethyl-benzyl)-2-(1'-methyl-[4,4']bipiperidinyl-1-yl)-2-oxo-ethyl 1',2'-dihydro-2'-oxospiro-4H-3', 1-benzoxazin-4,4'-piperidine-1-carboxylate, and (h) (R)-1-(4-amino-3-chloro-5-trifluoromethyl-benzyl)-2-[1,4']bipiperidinyl-1'-yl-2-oxo-ethyl 1',2'-dihydro-2'-oxospiro-4H-3',1-benzoxazin-4,4'-piperidine-1-carboxylate, or a tautomer or salt thereof.

3. A compound of the formula (I) according to claim 1, selected from the group consisting of:

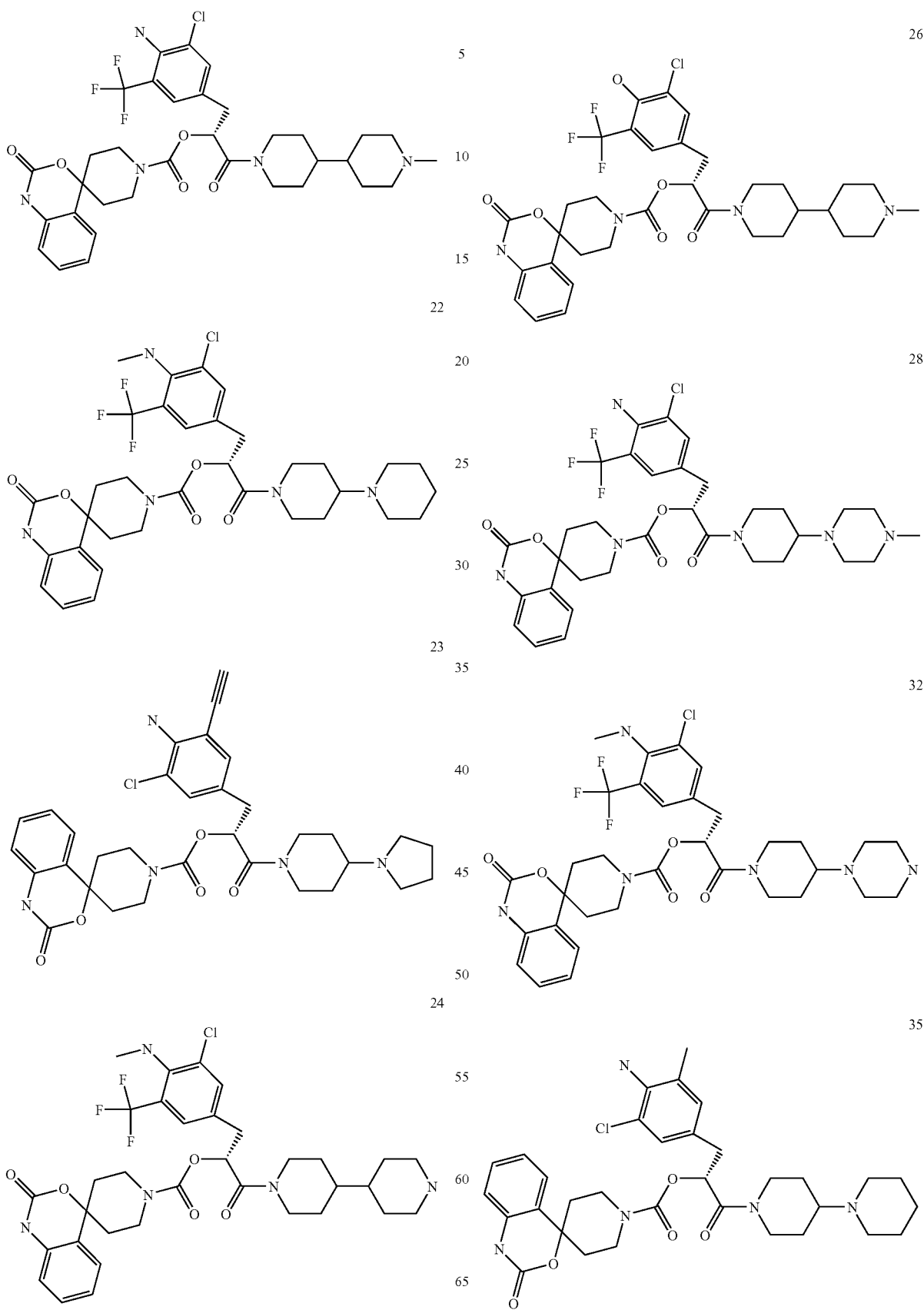

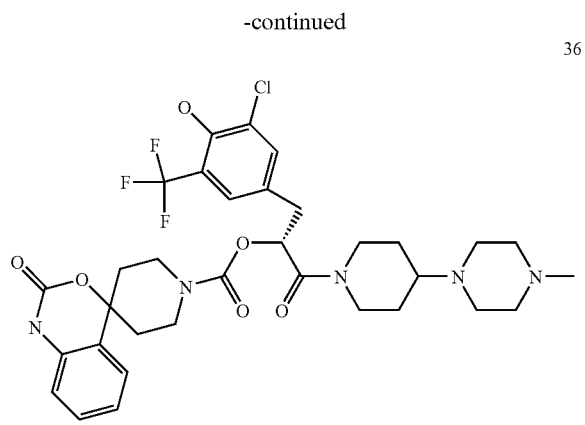
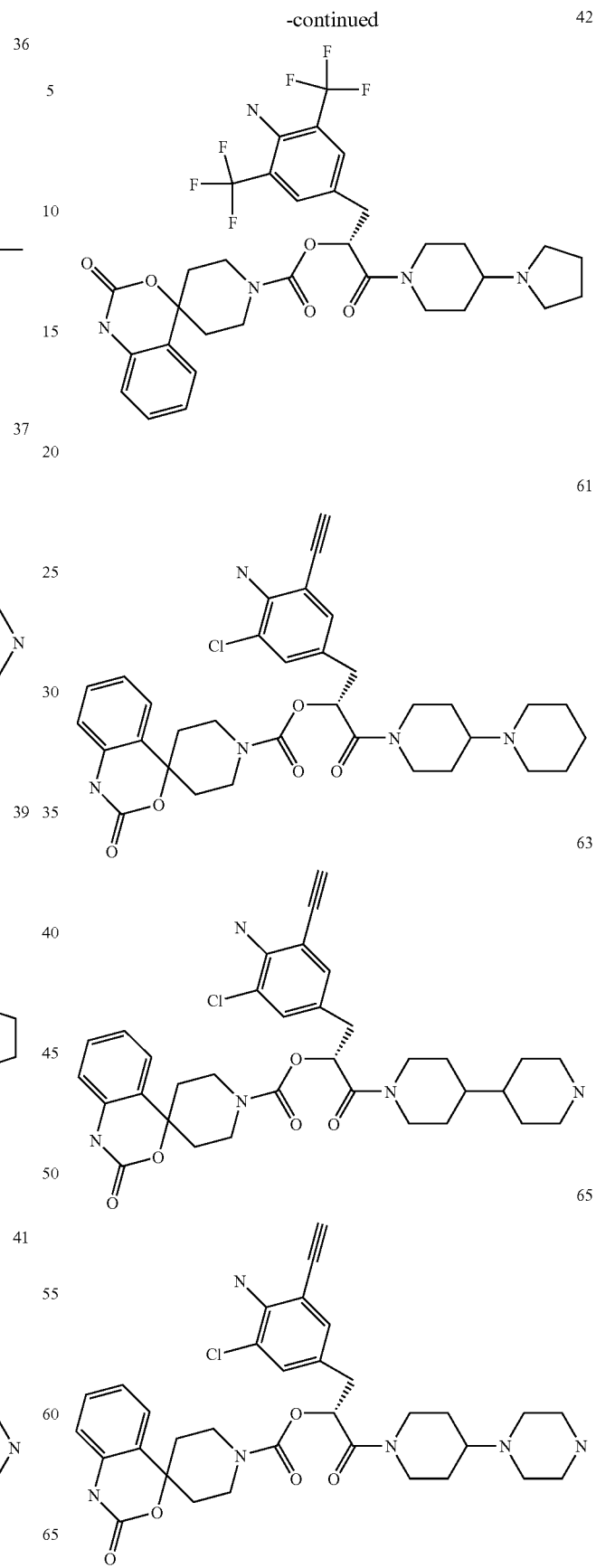

-continued
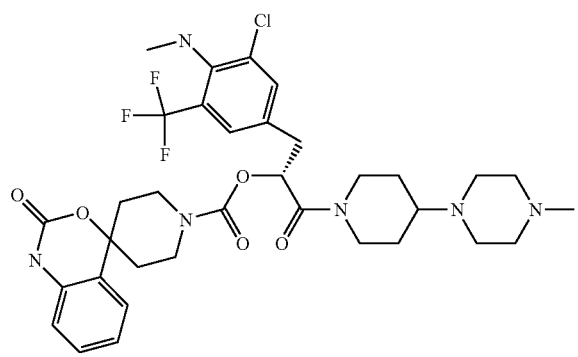
72
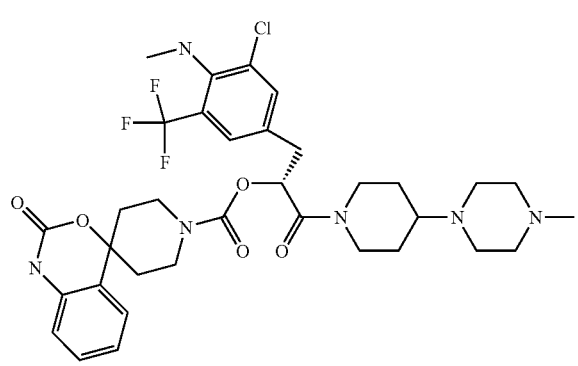
80
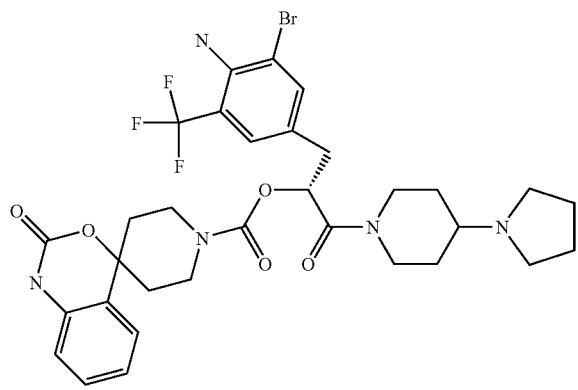
86
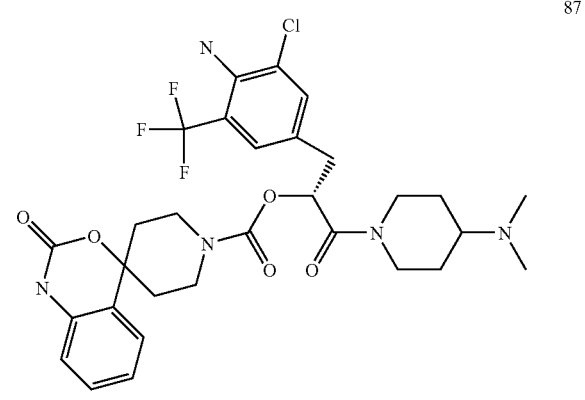
87
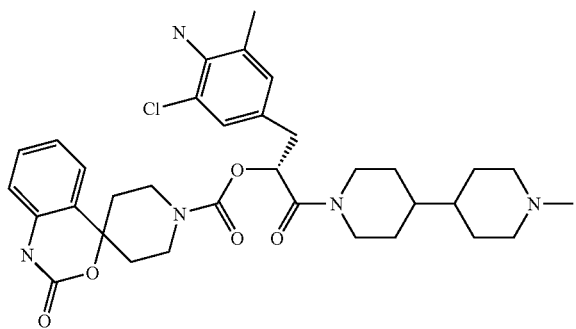
89

96
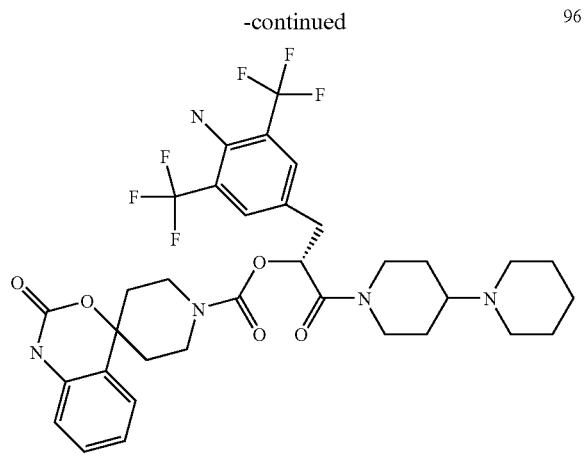
97
98
100
101
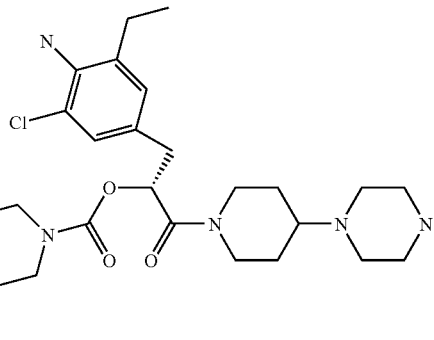
111
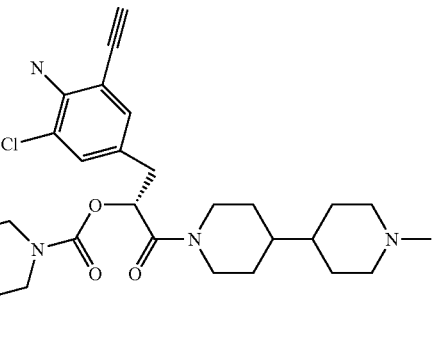
113
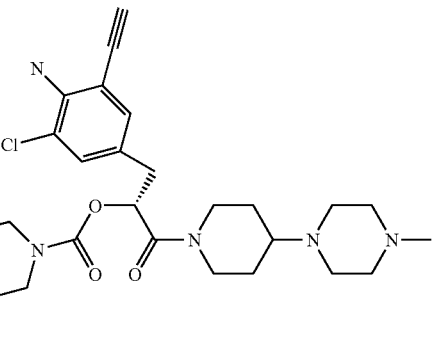
135
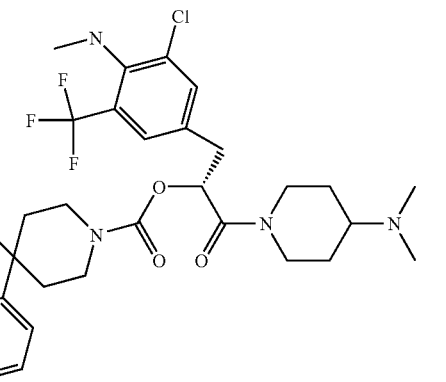

136
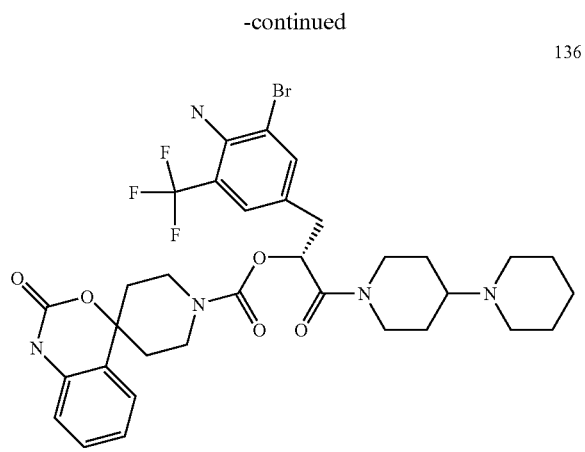
137
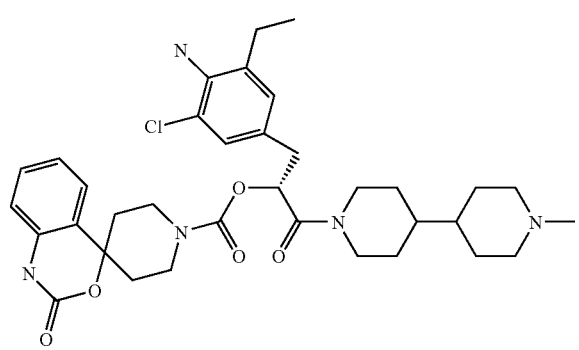
138
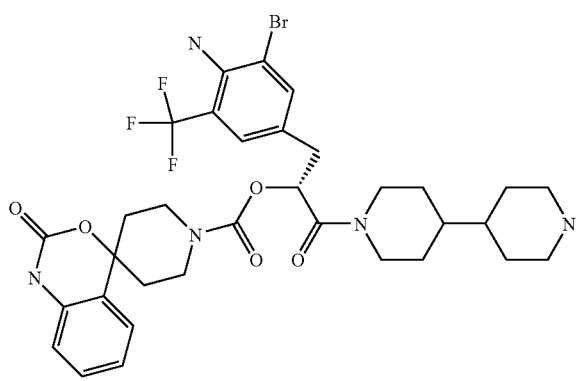
140
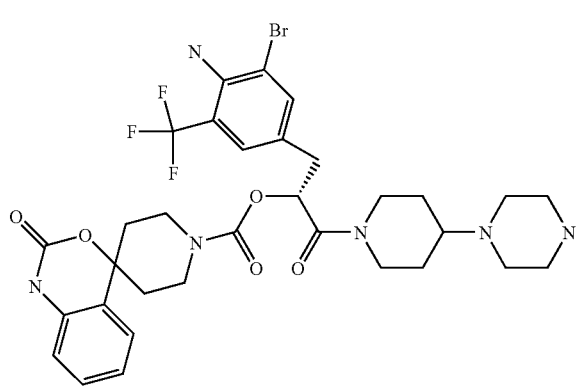
141
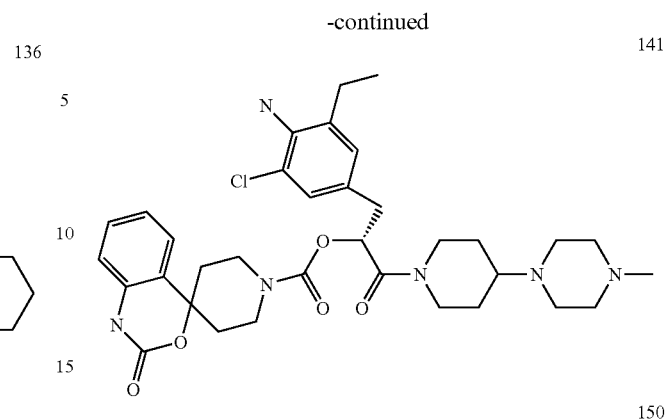
150
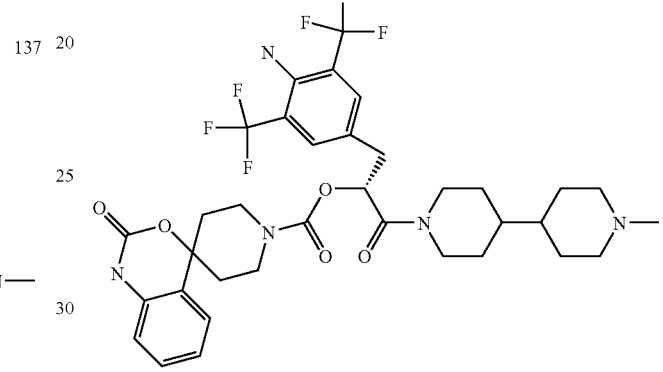
152
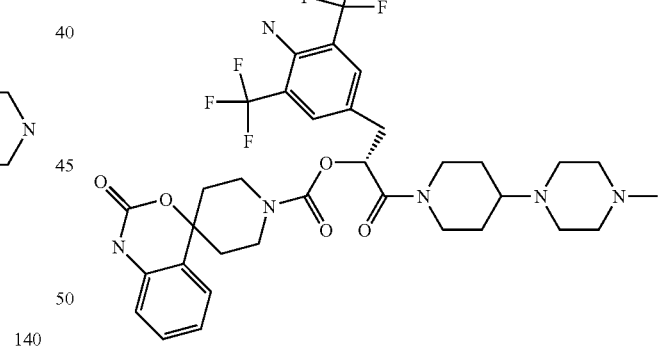
166
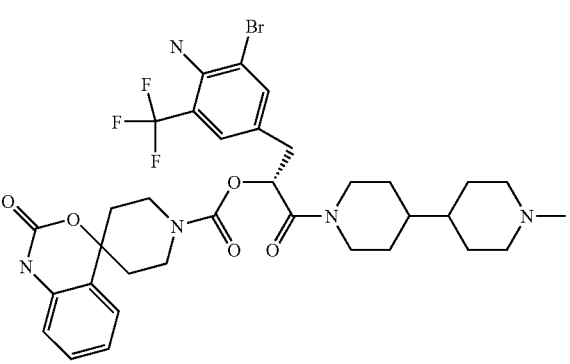

-continued
167
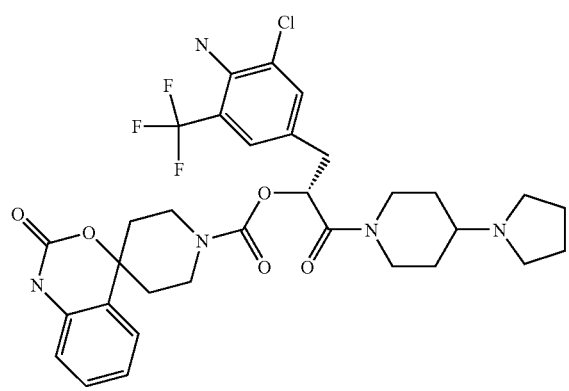
169
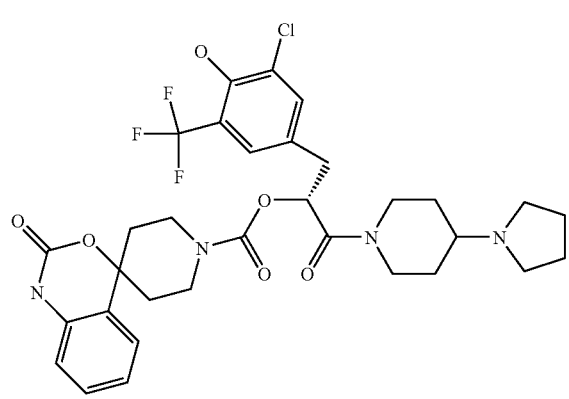
172
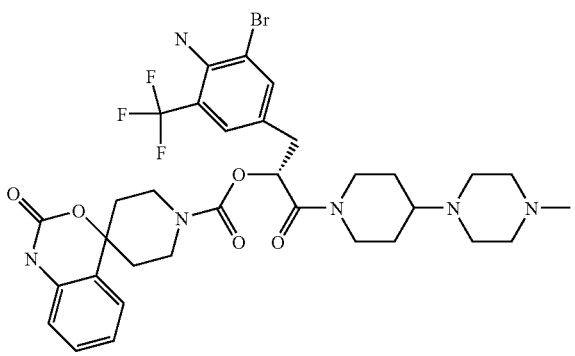
185
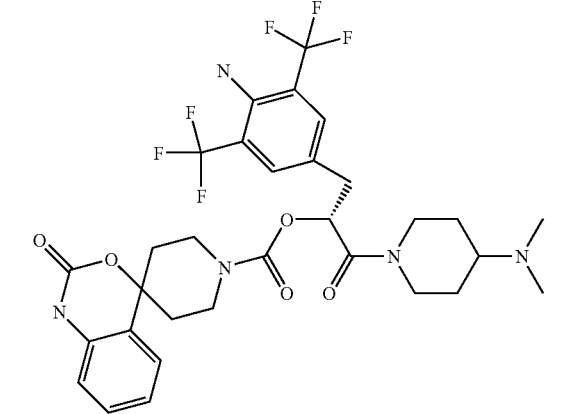
-continued
204
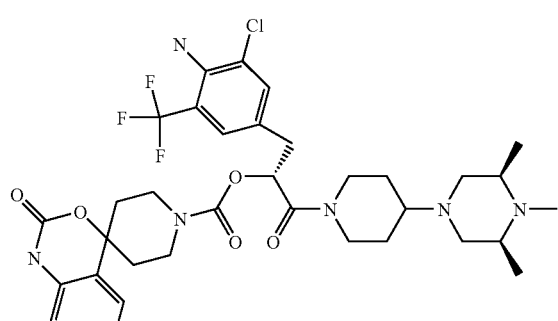
206
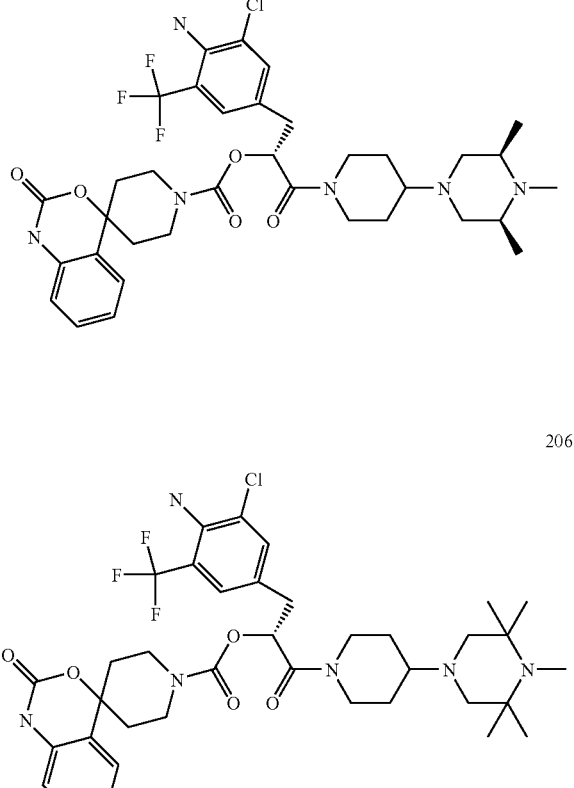
208
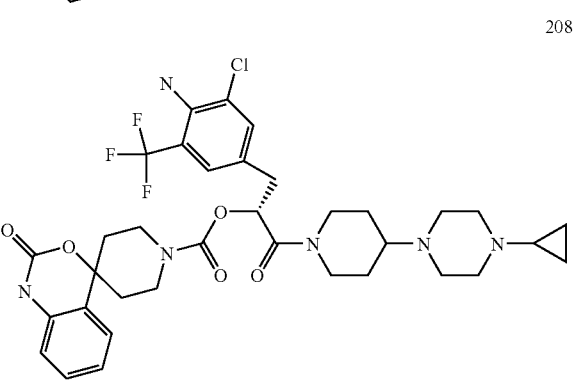
212
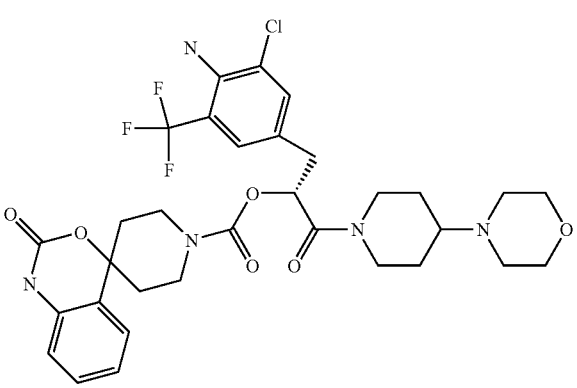

216 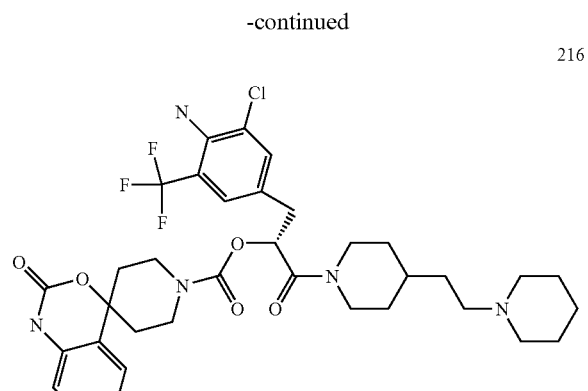
217 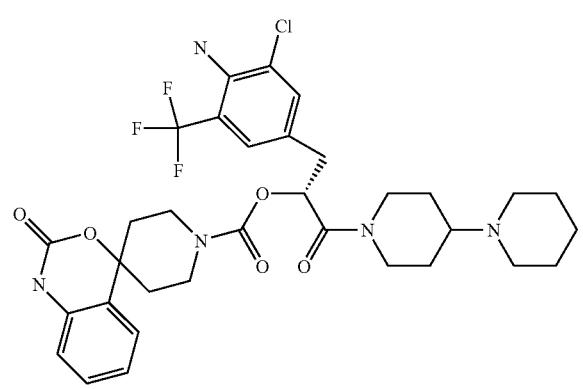
219 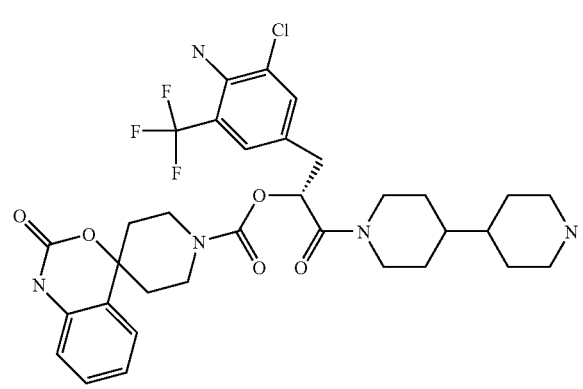
220 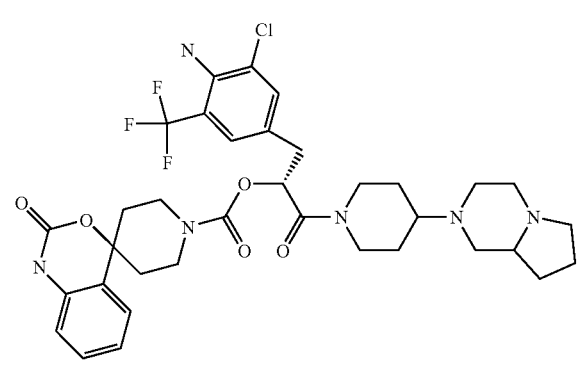
221 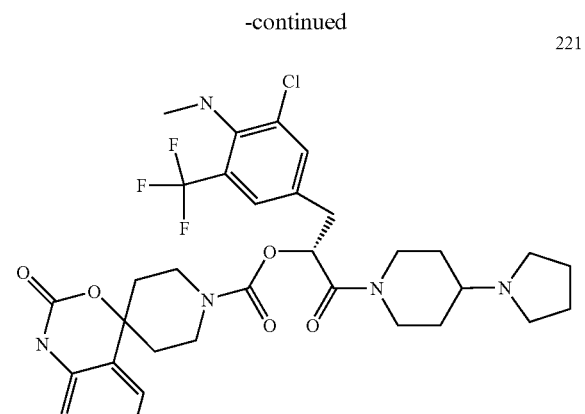
222 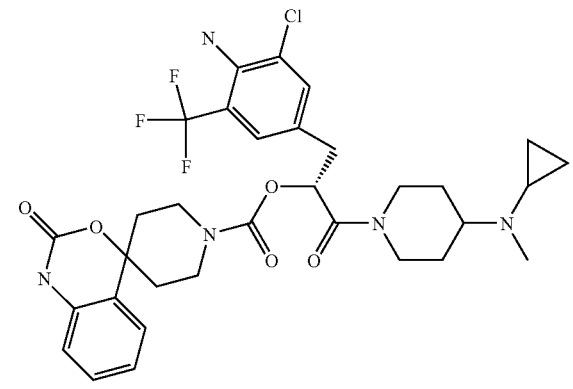
223 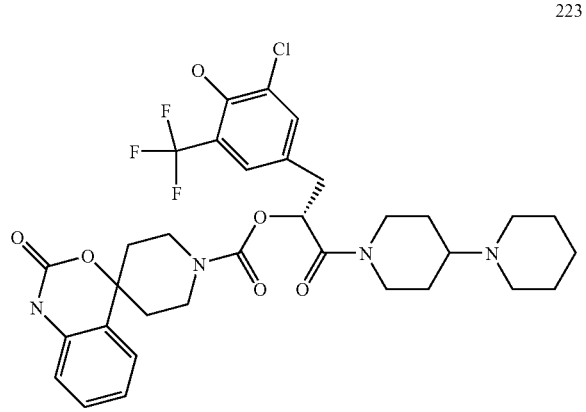
224 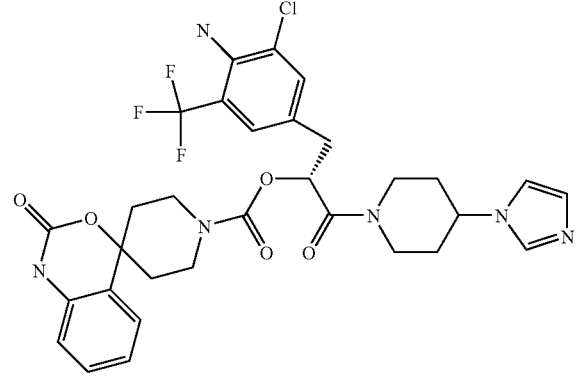

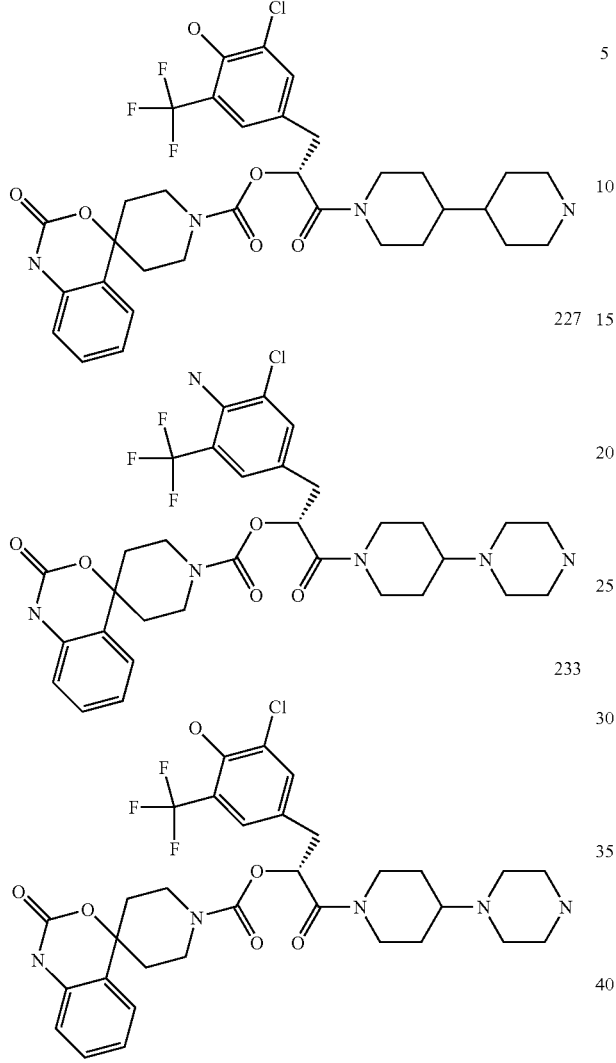

or a tautomer or salt thereof.

4. A physiologically acceptable salt of a compound according to claim 1, 2, or 3.

5. A pharmaceutical composition containing a compound according to claim 1, 2 or 3 or a physiologically acceptable salt thereof, together with one or more inert carriers and/or diluents.

6. A method for treating migraine or cluster headaches which comprises administering to a host in need of such treatment a therapeutically effective amount of a compound according to claim 1, 2 or a physiologically acceptable salt thereof.

7. A method for treating non-insulin-dependent diabetes mellitus (NIDDM) which comprises administering to a host in need of such treatment a therapeutically effective amount of a compound according to claim 1, 2 or a physiologically acceptable salt thereof.

* * * * *